(12) United States Patent
Abe et al.

(10) Patent No.: US 8,501,813 B2
(45) Date of Patent: Aug. 6, 2013

(54) γ-SECRETASE INHIBITOR

(75) Inventors: Atsuhiro Abe, Minato-ku (JP); Hideaki Shimizu, Minato-ku (JP); Seigo Sawada, Minato-ku (JP); Hiroshi Kodaira, Minato-ku (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 489 days.

(21) Appl. No.: 12/672,326

(22) PCT Filed: Jul. 1, 2008

(86) PCT No.: PCT/JP2008/001728
§ 371 (c)(1),
(2), (4) Date: Feb. 5, 2010

(87) PCT Pub. No.: WO2009/019815
PCT Pub. Date: Feb. 12, 2009

(65) Prior Publication Data
US 2011/0071224 A1    Mar. 24, 2011

(30) Foreign Application Priority Data
Aug. 9, 2007   (JP) ................. 2007-207521

(51) Int. Cl.
| A01N 37/18 | (2006.01) |
| A61K 31/16 | (2006.01) |
| C07C 233/00 | (2006.01) |
| C07C 235/00 | (2006.01) |
| C07C 237/00 | (2006.01) |
| C07C 239/00 | (2006.01) |

(52) U.S. Cl.
USPC .......................... 514/616; 564/153

(58) Field of Classification Search
USPC .......................... 514/616; 564/153
See application file for complete search history.

(56) References Cited

U.S. PATENT DOCUMENTS

| 2003/0092629 A1* | 5/2003 | Tang et al. ............ 514/13 |
| 2004/0121947 A1 | 6/2004 | Ghosh et al. |
| 2005/0239684 A1 | 10/2005 | Ghosh et al. |
| 2006/0205666 A1 | 9/2006 | Mori |
| 2010/0267609 A1 | 10/2010 | Ghosh et al. |

FOREIGN PATENT DOCUMENTS

| EP | 1 498 421 A1 | 1/2005 |
| WO | 02 053594 | 7/2002 |
| WO | WO 03/039454 A2 | 5/2003 |
| WO | WO 03/039454 A3 | 5/2003 |
| WO | 03 091278 | 11/2003 |

OTHER PUBLICATIONS

Churcher et al. "Gamma-secretase as a Therapeutic Target for the Treatment of Alzheimer's Disease", Current Pharmaceutical Design, 2005, vol. 11, pp. 3363-3382.*

Extended European Search Report issued Mar. 17, 2011, in Application No. / Patent No. 08790127.8-1216 / 2177529 PCT/JP2008001728.

Wolfe, M. S. et al., "A Substrate-Based Difluoro Ketone Selectively Inhibits Alzheimer's γ-Secretase Activity", Journal of Medicinal Chemistry, vol. 41, No. 1, pp. 6-9 (1998).

Shearman, M. S. et al., "L-685,458, An Aspartyl Protease Transition State Mimic, is a Potent Inhibitor of Amyloid β-Protein Precursor γ-Secretase Activity", Biochemistry, vol. 39 No. 30, pp. 8698-8704 (2000).

Nakajima, K. et al., " Mapping the Extended Substrate Binding Site of Cathepsin G and Human Leukocyte Elastase", The Journal of Biological Chemistry, vol. 254, No. 10, pp. 4027-4032, (1979).

* cited by examiner

*Primary Examiner* — Kendra D Carter
(74) *Attorney, Agent, or Firm* — Oblon, Spivak, McClelland, Maier & Neustadt, L.L.P.

(57) ABSTRACT

It is intended to provide a novel compound that has an excellent γ-secretase inhibitory effect and specifically inhibits Aβ production.

The present invention provides a compound of the following formula (1) or a pharmaceutically acceptable salt thereof: wherein $R^1$ represents a linear or branched alkyl group having 1 to 4 carbon atoms or a phenyl group; $R^2$ represents a linear or branched alkyl group having 1 to 4 carbon atoms which may be substituted by one or more phenyl or halogenophenyl groups; $R^3$ represents a linear or branched alkyl group having 1 to 4 carbon atoms which may be substituted by one or more hydroxyl groups; $R^4$ represents a linear or branched alkyl group having 1 to 4 carbon atoms; and the symbol "*" represents a chiral center.

(1)

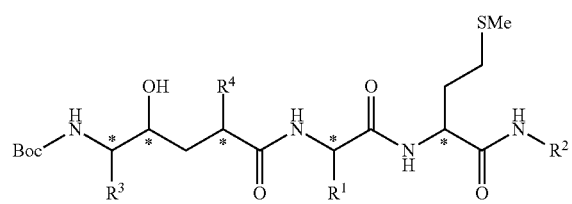

7 Claims, No Drawings

γ-SECRETASE INHIBITOR

This application is a National Stage of PCT/JP08/001,728 filed Jul. 1, 2008 and claims the benefit of JP 2007-207521 filed Aug. 9, 2007.

TECHNICAL FIELD

The present invention relates to a compound inhibiting γ-secretase, a proteinase that acts on amyloid precursor proteins to produce amyloid proteins, or a pharmaceutically acceptable salt thereof, and to a pharmaceutical agent containing the same.

BACKGROUND ART

With the advance of the aging society, the number of patients with Alzheimer-type dementia has increased in recent years, which has become a social problem.

The onset of Alzheimer-type dementia is considered to be deeply associated with the process of aggregation and accumulation following the enhanced production or reduced degradation of amyloid β proteins (hereinafter, referred to as Aβ), which are the main constituents of senile plaques characteristic of the brains of the patients.

This Aβ is composed of 40 to 42/43 amino acids rich in hydrophobic amino acids and produced from its precursor, amyloid precursor protein (hereinafter, referred to as APP) by hydrolytic cleavage. Moreover, APP is found as three isoforms: APP composed of 695 amino acids (hereinafter, referred to as APP695), APP composed of 751 amino acids (hereinafter, referred to as APP751), and APP composed of 770 amino acids (hereinafter, referred to as APP770).

The Aβ production from APP is performed through two-stage reaction, the first stage of which is β-secretase cleavage at the N-terminus in the extracellular domain and the second stage of which is γ-secretase cleavage at the C-terminus in the transmembrane region.

The previous findings have suggested that the cleavage at the second stage occurs at the C-terminal γ site of Aβ. However, according to the recent findings, it has been reported that the γ-secretase cleavage occurs nearer the cytoplasm, i.e., at the ε site (for APP770, $Thr_{719}$-$Leu_{720}$ or $Leu_{720}$-$Val_{721}$) 5 to 10 amino acid residues further downstream (C-terminal direction) from the γ site.

As currently known γ-secretase inhibitors, there have been reported, for example, a peptide mimetic DFK-167 based on the γ site of the substrate APP on which the enzyme acts (Non-Patent Document 1), a compound L-685,458 screened from among known inhibitors (Non-Patent Document 2), JLK-6 (Non-Patent Document 3), and a peptide mimetic based on the ε site (Patent Document 1).

However, the DFK-167 is an inhibitor designed for the γ site. Therefore, its design target and structure are totally different from those completed based on the recently reported findings about the ε site. Thus, the DFK-167 has the problem of an insufficient effect as an inhibitor.

Moreover, the L-685,458 and the α-chymotrypsin inhibitor JLK-6, which have been prepared during the course of the development of therapeutic drugs for AIDS, are not originally compounds developed as inhibitors specific to γ-secretase for Aβ production from APP. Therefore, they are insufficiently effective for the target tissue and have the problem that their nonspecific inhibition of γ-secretase activities might induce severe side effects such as induction of malignant transformation.

Furthermore, Patent Document 1 discloses a Thr-Leu-Val-Met-type compound as the peptide mimetic based on the ε site. However, this compound has the problem of an insufficient effect as an inhibitor. Examples of the document disclose a Thr-Leu-Val-Met-type compound (1'a) having a t-butyl-etherified hydroxyl group of Thr. However, this compound was merely a synthetic intermediate in a sense and was incomplete as the Thr-Leu-Val-Met-type compound.

In addition, a Thr-Leu-Val-Met-type compound having an unprotected hydroxyl group of Thr and the specific γ-secretase inhibitory effect of the compound have been unknown so far.

Patent Document 1: WO03/091278
Non-Patent Document 1: J. Med. Chem., 1998, 41 (1), 6-9
Non-Patent Document 2: Biochemistry, 2000, 39 (30), 8698-8704
Non-Patent Document 3: J. Biol. Chem., 1979, 254 (10), 4027-4032

DISCLOSURE OF THE INVENTION

Problems to be Solved by the Invention

Thus, an object of the present invention is to provide a novel compound that has an excellent γ-secretase inhibitory effect and specifically inhibits Aβ production.

A further object of the present invention is to provide a therapeutic drug and a therapeutic method, etc., useful for Alzheimer's disease and diseases related thereto. In this context, the diseases related thereto refer to Down's syndrome or other diseases known to directly or indirectly involve Aβ as a cause thereof or suspected of having the possibility of such involvement, and diseases whose nerve lesions contain detectable Aβ.

Means for Solving the Problems

The present invention has been completed by finding, as a result of inventive approaches to focus on the ε site of APP in the light of findings from related studies, that the dramatic and efficient inhibition of γ-secretase and the inhibition of Aβ production are achieved using a peptide mimetic with a particular structure, which is similar in chemical structure to a four-amino acid sequence (Thr-Leu-Val-Met) containing the ε site of APP and has a bond stable to the enzyme, substituted for the peptide bond between Thr and Leu at the enzymatic cleavage site ε site.

Specifically, the present invention provides a compound of the following formula (1) or a pharmaceutically acceptable salt thereof:

[Formula 1]

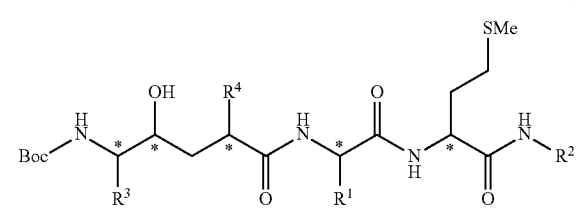

wherein $R^1$ represents a linear or branched alkyl group having 1 to 4 carbon atoms or a phenyl group; $R^2$ represents a linear or branched alkyl group having 1 to 4 carbon atoms which may be substituted by one or more phenyl or halogenophenyl groups; $R^3$ represents a linear or branched alkyl group having 1 to 4 carbon atoms which may be substituted by one or more hydroxyl groups; $R^4$ represents a linear or branched alkyl group having 1 to 4 carbon atoms; and the symbol "*" represents a chiral center.

The present invention also provides a pharmaceutical agent containing the compound of the formula (1) or a pharmaceutically acceptable salt thereof.

The present invention also provides a γ-secretase inhibitor containing the compound of the formula (1) or a pharmaceutically acceptable salt thereof.

The present invention also provides an amyloid protein production inhibitor containing the compound of the formula (1) or a pharmaceutically acceptable salt thereof.

The present invention also provides a preventive/therapeutic agent for disease involving γ-secretase, containing the compound of the formula (1) or a pharmaceutically acceptable salt thereof.

The present invention also provides use of the compound of the formula (1) or a pharmaceutically acceptable salt thereof for production of a γ-secretase inhibitor, an amyloid protein production inhibitor, or a preventive/therapeutic agent for disease involving γ-secretase.

The present invention also provides a method for inhibiting γ-secretase, a method for inhibiting amyloid protein production, or a preventive/therapeutic method for disease involving γ-secretase, comprising using the compound of the formula (1) or a pharmaceutically acceptable salt thereof.

Effects of the Invention

A compound of the present invention and a pharmaceutically acceptable salt thereof can be used in the prevention/treatment of Alzheimer's disease and diseases related thereto, for example, Down's syndrome or other diseases known to directly or indirectly involve Aβ as a cause thereof or suspected of having the possibility of such involvement, and diseases whose nerve lesions contain detectable Aβ.

Moreover, the compound of the present invention and the pharmaceutically acceptable salt thereof have the activity of specifically inhibiting Aβ production and can be used effectively and safely according to the preventive/therapeutic purpose for the diseases.

BEST MODE FOR CARRYING OUT THE INVENTION

In the present invention, a compound of the formula (1) contains at least five chiral centers (in the formula, the chiral center is represented by the symbol "*") and can be found in various enantiomeric or diastereomeric forms, since these chiral centers can assume any of R and S configurations. Racemic mixtures of such compounds as well as all optical isomers and all stereoisomers both as individual enantiomers/diastereomers and as mixtures thereof are encompassed by the scope of the present invention. Examples of the isomers include (2R,4R)-, (2R,4S)-, (2S,4R)-, and (2S,4S)-isomers. The (2R,4R)-isomer is particularly preferable from the viewpoint of strongly inhibiting γ-secretase and specifically inhibiting Aβ production.

In the present invention, $R^1$ represents a linear or branched alkyl group having 1 to 4 carbon atoms or a phenyl group. Examples of the linear or branched alkyl group having 1 to 4 carbon atoms include methyl, ethyl, propyl, isopropyl, n-butyl, sec-butyl, and t-butyl groups. $R^1$ is particularly preferably the methyl, isopropyl, or phenyl group.

In the present invention, $R^2$ represents a linear or branched alkyl group having 1 to 4 carbon atoms which may be substituted by one or more phenyl or halogenophenyl groups. Examples of the linear or branched alkyl group having 1 to 4 carbon atoms include methyl, ethyl, propyl, isopropyl, n-butyl, sec-butyl, and t-butyl groups. In particular, the methyl, ethyl, or n-butyl group is preferable.

Moreover, preferable examples of the linear or branched alkyl group having 1 to 4 carbon atoms which may be substituted by one or more phenyl groups include benzyl and 1-phenyl-ethyl groups.

Examples of a halogen atom in the halogenophenyl groups include fluorine, chlorine, bromine, and iodine. The fluorine is preferable. One preferable example of the linear or branched alkyl group having 1 to 4 carbon atoms which may be substituted by halogenophenyl groups includes a 4-fluorobenzyl group.

In the present invention, $R^3$ represents a linear or branched alkyl group having 1 to 4 carbon atoms which may be substituted by one or more hydroxyl groups. Specific examples thereof include 1-hydroxyethyl and hydroxymethyl groups. In particular, the 1-hydroxyethyl group is preferable.

In the present invention, $R^4$ represents a linear or branched alkyl group having 1 to 4 carbon atoms. Specific examples thereof include isobutyl and sec-butyl groups. In particular, the isobutyl group is preferable.

In the present invention, a compound of the following formula (2) or a pharmaceutically acceptable salt thereof is more preferable from the viewpoint of strongly inhibiting γ-secretase and specifically inhibiting Aβ production:

[Formula 2]

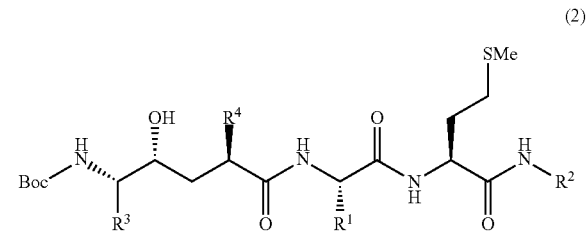

wherein $R^1$, $R^2$, $R^3$, and $R^4$ are as defined above.

In the present invention, a compound of the following formula (3) or a pharmaceutically acceptable salt thereof is even more preferable from the viewpoint of strongly inhibiting γ-secretase and specifically inhibiting Aβ production:

[Formula 3]

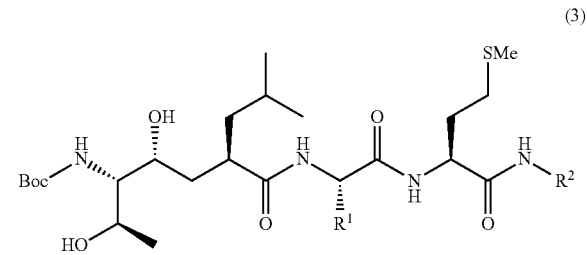

wherein $R^1$ and $R^2$ are as defined above.

In the present invention, the following compounds and pharmaceutically acceptable salts thereof are particularly preferable:

[5S-(tert-butoxycarbonylamino)-4R,6R-dihydroxy-2R-(2-methylpropyl)heptanoyl]-L-valyl-L-methionine benzylamide (TLVM-5),

[5S-(tert-butoxycarbonylamino)-4R,6R-dihydroxy-2R-(2-methylpropyl)heptanoyl]-L-valyl-L-methionine n-butylamide (TLVM-7),

[5S-(tert-butoxycarbonylamino)-4R,6R-dihydroxy-2R-(2-methylpropyl)heptanoyl]-L-valyl-L-methionine (S)-α-methylbenzylamide (TLVM-8),

[5S-(tert-butoxycarbonylamino)-4R,6R-dihydroxy-2R-(2-methylpropyl)heptanoyl]-L-valyl-L-methionine 4-fluorobenzylamide (TLVM-9),

[5S-(tert-butoxycarbonylamino)-4R,6R-dihydroxy-2R-(2-methylpropyl)heptanoyl]-L-alanyl-L-methionine benzylamide (TLVM-10), and

[5S-(tert-butoxycarbonylamino)-4R,6R-dihydroxy-2R-(2-methylpropyl)heptanoyl]-L-phenylglycyl-L-methionine benzylamide (TLVM-11).

In the present invention, examples of the pharmaceutically acceptable salt include: acid addition salts such as hydrochloride, sulfate, citrate, tartrate, acetate, methanesulfonate, phosphate, oxalate, benzoate, trifluoroacetate, maleate, fumarate, lactate, bromate, iodate, succinate, and glutarate; and metal salts such as lithium salts, sodium salts, potassium salts, and magnesium salts.

In the present invention, the "amyloid protein production inhibitor" means, of various type I membrane proteins serving as substrates for γ-secretase, a compound that has an inhibitory effect on Aβ production and has no inhibitory effect on production of other membrane proteins (e.g., human Alcadein) as the substrates. More specifically, it means a compound that brings about (i) an Aβ secretion rate of 50% or less and (ii) an Alcadein secretion rate of 60% or more, respectively, determined by methods described later (Example 11) and further brings about (i)/(ii) of 0.8 or less, more preferably 0.4 or less.

In the light of the results of previous detailed studies on degradation products of APP, the peptide mimetic of the present invention was obtained from an attempt to create a compound that is similar in structure to the ε site and is stabilized against the enzyme, on the assumption that γ-secretase activities can be inhibited by stabilizing the ε site against the enzyme. The peptide mimetic of the present invention can be used as an inhibitor not only for Aβ production in sporadic Alzheimer's disease but for Aβ production having a genetic variation that causes early-onset familial Alzheimer's disease.

Of various peptide analogs similar in amino acid sequence to the ε site of APP and its neighborhood and modified to stabilize the γ-secretase cleavage site, those having γ-secretase inhibitory activities can be used for the purposes of the present invention. Examples of such compounds include compounds having γ-secretase inhibitory activities in a form where a certain amino acid residue —NH—CHR—CO— in the neighborhood of the ε site is substituted by another amino acid residue similar in the property of the moiety R thereto (hydrophobicity/hydrophilicity, acidity/basicity, the presence or absence of sulfur, the presence or absence of a hydroxyl group, etc.). Examples of amino acids that can be used in the substitution include: for Leu, Ile, Val, Ala, and Gly; for Thr, Ser; for Met, Ala; and for Val, Leu, Ala, Gly, Ile, t-butylglycine, norleucine, norvaline, phenylglycine, and 2-aminobutyric acid.

Materials for synthesizing the compound of the present invention and methods used in each step of the synthesis are well known. Therefore, those skilled in the art can appropriately produce the compound of interest by appropriately performing synthesis, isolation, purification, and so on. Moreover, the polypeptide portion in the compound of the present invention may be produced by a gene recombination technique using hosts known per se in the art such as *E. coli*, yeast, *Bacillus subtilis*, insect cells, animal cells, and plant cells. The chemical synthesis can be performed, for example, according to Examples described later. However, any method may be used as long as the compound of interest is obtained. The compound can be obtained by appropriately combining well-known methods, for example, Boc (tert-butoxycarbonyl) reaction, DMSO oxidation, alkali reaction, acid reaction, epoxidation, silica gel column chromatography, alkylation, saponification, thermal reaction, decarboxylation, condensation, reverse-phase high-performance liquid chromatography, acylation, transfer reaction, isomerization, metathesis reaction, addition reaction, oxidation, reduction, halogenation, radical reaction, coupling reaction, elimination, nitration, and sulfonation. Preferably, a method is adopted, which includes sequentially reacting structural element portions of the compound of the present invention and appropriately conducting assay on efficiency and purity of the reaction products.

The compound of the present invention may contain a modification for promoting synthesis or purification, a modification for promoting physical/chemical stabilization, an activation modification such as in vivo metabolic stability and instability and in vivo metabolic conditioning, and a controlled modification that enhances or reduces the transport efficiency to organs including crossing of the blood-brain barrier. In this context, the controlled modification represents a sequence of 11 amino acids Tyr-Gly-Arg-Lys-Lys-Arg-Arg-Gln-Arg-Arg-Arg. The compound, which contains the controlled sequence linked through a peptide bond to the N terminus, can cross the blood-brain barrier more easily and arrive more efficiently at the target site in the brain.

Examples of other modifications for the compound of the present invention include acetylation, acylation, ADP-ribosylation, amidation, covalent bonding with flavin, covalent bonding with a heme portion, covalent bonding with a nucleotide or a nucleotide derivative, covalent bonding with a lipid or a lipid derivative, covalent bonding with phosphatidylinositol, cross-linking, cyclization, disulfide bonding, demethylation, covalent cross-link formation, cystine formation, pyroglutamate formation, formylation, gamma-carboxylation, glycosylation, GPI-anchoring, hydroxylation, iodation, methylation, myristoylation, oxidation, proteolytic processing, phosphorylation, prenylation, racemization, lipid binding, sulfation, selenoylation, transfer RNA-mediate addition of amino acids to proteins (e.g., arginylation), ubiquitination, dehydration condensation, and alkoxycarbonylation.

Furthermore, for facilitating the detection or purification of the compound of the present invention or for imparting an additional function thereto, the addition, modification, substitution of the structure is technically performed with ease. The resulting products are also encompassed by the scope of the present invention. In this context, products obtained by genetic engineering approaches such as the addition of a modification with FLAG-tag, β-galactosidase, alkaline phosphatase, immunoglobulin (e.g., IgG) Fc fragments, or GFP are also encompassed by the scope of the present invention.

Furthermore, an antibody against the compound of the present invention can be prepared, if necessary. The antibody can be purified by screening the compound of the present invention, a derivative thereof, or a degradation product thereof and using it as an antigen. The antigen may be the compound or a derivative thereof and is composed of, for example, 4 or less amino acid residues, preferably 3 or less amino acid residues, even more preferably 2 amino acid residues. In the purification, these antigens may be combined for use. The antigen is not necessarily required to be the compound of the present invention, the derivative thereof, or the degradation product thereof in itself and needs only to be a compound having a primary sequence proximal to the ε site of APP, which is exposed on the surface in terms of the three-dimensional structure. The antibody is not particularly limited in type and amount as long as it immunologically binds to the site or recognizes this site. The presence or absence of the binding or recognition of the antibody is determined based on antigen-antibody reaction known in the art.

The antibody is produced by using the compound of the present invention, the derivative thereof, or the degradation product thereof as an antigen and inducing humoral-mediated and/or cell-mediated immunity against the antigen alone or as a conjugate or in coexistence with a carrier in the presence or absence of an adjuvant. Alternatively, the induction of immunity can also be performed by immunologically stimulating lymphocytes or precursor cells thereof under culture conditions. The carrier is not particularly limited unless the carrier itself adversely affects hosts. Examples thereof include, but not limited to, cellulose, saline, buffered saline, dextrose, water, glycerol, ethanol, polymerized amino acids, albumin, and mixtures thereof. Mice, rats, rabbits, goats, horses, cow, and the like are preferably used as animals to be immunized. Polyclonal antibodies are obtained as serum by a method known per se in the art or by an antibody collection method from the serum. Preferable examples of means therefor include immunoaffinity chromatography.

Monoclonal antibodies are produced by collecting tissue (e.g., spleen or lymph node) or cultured cells containing antibody activities, from the animals thus immunized and adopting means for transformation to immortalized cells (e.g., myeloma strains such as P3X63Ag8 strains) known per se in the art. For example, hybridomas prepared from the antibody-producing cells and the immortalized cells are cloned, and hybridomas that produce an antibody specifically recognizing the novel compound according to the present invention are screened. The antibody is collected from a culture solution of the hybridomas. By way of illustration, various techniques are described in, for example, the hybridoma method (Kohler G. and Milstein C. (1975) Nature 256, 495-497), the trioma method (Kozbor et al., Immunology Today (1983) 4: 72), and the EBV method (Cole et al., Monoclonal antibodies and cancer therapy, Alan R. Liss, Inc., (1985): 77-96).

The antibody can be used in the identification, detection, or quantification of the compound of the present invention, the derivative thereof, or the degradation product thereof or in the preparation and purification of the compound by affinity chromatography. The antibody can be modified to a human antibody using an approach known per se in the art.

Specifically, the compound of the present invention, the derivative thereof, or the degradation product thereof, and the specific antibody thereagainst having the activity of increasing the activities of the compound of the present invention, the derivative thereof, or the degradation product thereof are useful as standards for compounds subjected to screening of an Aβ production inhibitor or as screening means.

Examples of assay using the antibody against the compound of the present invention, the derivative thereof, or the degradation product thereof include radioimmunoassay, competitive binding assay, high-performance liquid chromatography, western blot analysis, and ELISA assay, and combinations thereof.

The compound of the present invention is used for the prevention, treatment, and symptomatic improvement of Alzheimer's disease and diseases related thereto by administering the compound alone or in a pharmaceutically acceptable carrier in an amount effective for these diseases to a patient to control the amount of Aβ produced. The compound of the present invention may be made into an appropriate preparation that enhances the transport efficiency of the compound to brain tissues. In this context, examples of the Alzheimer's disease and the diseases related thereto include Alzheimer's disease, Creutzfeldt-Jakob disease, prion disorder, amyotrophic lateral sclerosis, progressive supranuclear palsy, head injury, stroke, Down's syndrome, pancreatitis, inclusion body myositis, other peripheral amyloidoses, and diabetes mellitus.

The compounds of the present invention may be used alone or in combination of two or more thereof. Furthermore, the compound of the present invention may be used in combination with an additional compound with therapeutic advantage. The additional compound may have the same or different mechanism of action as or from that of the compound of the present invention. The systemic dosage form of a pharmaceutical composition containing the compound of the present invention is preferably injection, particularly preferably intravenous injection. Other injection routes can also be used, such as subcutaneous, intramuscular, and intraperitoneal injections. Another means for the systemic administration is transmucosal or transdermal administration using a penetrant such as bile salt, fusidic acid, or other surfactants. Furthermore, oral administration may be performed using enteric-coated formulation or capsule formulation or the like. These pharmaceutical compositions may be locally administered and may be in the form of ointments, pastes, gels, and the like.

The dose of the peptide analog used as an active ingredient of the γ-secretase inhibitor of the present invention is not strictly limited. It is preferred to set an appropriate dose, because the obtained effects differ depending on various modes of use in the target individual, the applicable disease, etc. The preferable dose thereof is 0.01 to 100 g, more preferably 0.1 to 10 g, per day.

Examples of such preparations include: solid formulations such as tablets, granules, powders, and capsules; liquid formulations such as solutions, suspensions, and emulsions; and freeze-dried formulations. These preparations can be prepared according to usual pharmaceutical practice. Examples of the nontoxic pharmaceutical carrier include starch, dextrin, fatty acid glyceride, polyethylene glycol, hydroxyethyl starch, ethylene glycol, polyoxyethylene sorbitan fatty acid ester, amino acids, gelatin, albumin, water, and saline. Moreover, additives commonly used such as stabilizers, humectants, emulsifying agents, binders, tonicity agents, and excipients can also be added appropriately thereto, if necessary.

Moreover, the γ-secretase inhibitor of the present invention can be used not only as such a pharmaceutical preparation but also as a food or drink or the like. In this case, the peptide analog of the present invention may be contained alone or as a mixture supplemented with various nutrients in a food or drink. This food or drink can be used as a supplement food or food ingredient useful for the improvement, prevention, and so on of Alzheimer's disease, Creutzfeldt-Jakob disease, prion disorder, amyotrophic lateral sclerosis, progressive supranuclear palsy, head injury, stroke, Down's syndrome, pancreatitis, inclusion body myositis, other peripheral amyloidoses, and diabetes mellitus, and the like. This food or drink or a container thereof may be provided with an indication that states it has the effects described above. Specifically, when the γ-secretase inhibitor of the present invention is formulated into a food or drink, the γ-secretase inhibitor may be molded into a form suitable for foods, for example, granule, powder, tablet, capsule, and paste forms, according to means commonly used, appropriately using additives available in foods and drinks, and may be added, for use, to various foods, for example, processed meat (e.g., ham and sausage), processed marine products (e.g., kamaboko (steamed fish paste) and chikuwa (fish sausage)), bread, confectionery, butter, powdered milk, and fermented foods and drinks or to drinks, for example, water, fruit juice, milk, soft drinks, and tea drinks. In this context, animal feed is also included in the food or drink.

Furthermore, fermented dairy products such as fermented milk, lactic acid bacteria beverages, fermented soy milk, fermented fruit juice, and fermented vegetable juice, containing the peptide analog as an active ingredient are preferably used as the food or drink. These fermented foods and drinks can be produced according to a standard method. For example, for the fermented milk, a lactic acid bacterium or *bifidobacterium* may be inoculated to a sterilized milk medium and cultured, and the culture is homogenized to obtain a fermented milk base. Subsequently, a separately prepared syrup solution and the peptide analog are added thereto and mixed, and the mixture is homogenized using a homogenizer or the like, to which a flavor is further added to obtain the final product. The fermented milk thus obtained may be made into products in any form such as plane type, soft type, fruit flavor type, solid form, and liquid form.

Moreover, the γ-secretase inhibitor of the present invention can be applied to all mammals including humans.

EXAMPLES

Hereinafter, the contents of the present invention will be described in more detail with reference to Examples. However, the present invention is not intended to be limited to them by any means.

Example 1

Production of [5S-(tert-butoxycarbonylamino)-4S, 6R-dihydroxy-2R-(2-methylpropyl)heptanoyl]-L-valyl-L-methionine benzylamide (TLVM-4)

(Step 1)

3-Benzyloxycarbonyl-2,2-dimethyl-4S-(N-methoxy-N-methylcarbamoyl)-5R-methyloxazolidine (compound 1)

N-Cbz-L-threonine (12.7 g, 50 mmol), dimethylhydroxylamine hydrochloride (5.9 g, 60 mmol), and EDC hydrochloride (11.5 g, 60 mmol) were dissolved in chloroform (350 ml). To the solution, triethylamine (8.4 ml, 60 mmol) and HOBt.H$_2$O (7.7 g, 50 mmol) were added, and the mixture was stirred at 40° C. for 6 days. To the reaction mixture, ethyl acetate was added, and the organic layer was washed with 1 N hydrochloric acid, water, and an aqueous solution of saturated sodium bicarbonate and then dried over anhydrous magnesium sulfate. The solvent was distilled off under reduced pressure. The residue (12.4 g) was dissolved in toluene (250 ml). To the solution, 2-methoxypropene (35 ml) and PPTS (0.39 g) were added, and the mixture was stirred at 80° C. for 2 hours. The toluene was distilled off. Then, to the residue, chloroform was added, and the organic layer was washed with an aqueous solution of saturated sodium bicarbonate. The organic layer was dried over anhydrous magnesium sulfate, and the solvent was distilled off under reduced pressure. Then, the residue was purified by silica gel column chromatography (hexane:AcOEt=8:1 to 4:1) to obtain the title compound (12.2 g, 36 mmol, 80%).

$^1$H-NMR (CDCl$_3$) δ: 1.36 and 1.40 (3H, 2 d, J=6 Hz) 1.60 and 1.68 (3H, 2 s) 1.62 and 1.71 (3H, 2 s) 3.02 (3H, s) 3.24 and 3.26 (3H, 2 s) 4.15 and 4.22 (1H, 2 m) 4.39 and 4.57 (1H, 2 d, J=7 Hz) 4.92 and 5.12 (1H, 2 d, J=12 Hz) 5.09 and 5.20 (1H, 2 d, J=12 Hz) 7.28-7.38 (5H, m).

(Step 2)

3-Benzyloxycarbonyl-2,2-dimethyl-4S-(4-pentenoyl)-5R-methyloxazolidine (compound 2)

The compound 1 (12.2 g, 36 mmol) was dissolved in THF (170 ml). To the solution, 3-butenyl magnesium bromide (0.5 mol/l THF solution, 130 ml, 65 mmol) was added dropwise in an ice bath, and the mixture was stirred for 0.5 hours in an ice bath and then stirred at room temperature for 3 days. To the reaction mixture, an aqueous citric acid solution was added, and the mixture was stirred for 10 minutes, followed by extraction with chloroform. The organic layer was dried over anhydrous magnesium sulfate, and the solvent was distilled off under reduced pressure. Then, the residue was purified by silica gel column chromatography (hexane:AcOEt=9:1 to 6:1) to obtain the title compound (6.9 g, 20.8 mmol, 78%) and an unreacted compound 1 (3.14 g, 9.3 mmol).

$^1$H-NMR (CDCl$_3$) δ: 1.37 and 1.38 (3H, 2 d, J=5 Hz) 1.56 and 1.68 (3H, 2 s) 1.57 and 1.62 (3H, 2 s) 2.05-2.85 (4H, m) 3.96-4.15 (2H, m) 4.88-5.17 (2H, m) 4.98 and 5.12 (1H, 2 d, J=12 Hz) 5.06 and 5.16 (1H, 2 d, J=12 Hz) 5.60 and 5.80 (1H, 2 m) 7.28-7.38 (5H, m).

(Step 3)

4-(3-Benzyloxycarbonyl-2,2-dimethyl-5R-methyloxazolidin-4S-yl)-4-oxobutyric acid (compound 3)

The compound 2 (6.9 g, 21 mmol) was dissolved in toluene (105 ml). To the solution, nBu$_4$NBr (84 mg), water (105 ml), and acetic acid (21 ml) were added. The mixture was stirred for 10 minutes in an ice bath. Then, KMnO$_4$ (11.3 g, 71.4 mmol) was added thereto, and the mixture was vigorously stirred at room temperature for 5 hours. To the reaction mixture, NaHSO$_3$ was added, and the pH of the mixture was then adjusted to 1 to 2 by the addition of an aqueous solution of saturated potassium bisulfate in an ice bath. After extraction with chloroform, the organic layer was dried over anhydrous magnesium sulfate, and the solvent was distilled off under reduced pressure. Then, the residue was purified by silica gel column chromatography (hexane:AcOEt=8:1 to CHCl$_3$:MeOH=97:3) to obtain the title compound (5.2 g, 14.9 mmol, 83%) and an unreacted compound 2 (1.02 g, 3.1 mmol).

$^1$H-NMR (CDCl$_3$) δ: 1.38 and 1.41 (3H, 2 d, J=5 Hz) 1.57 and 1.63 (3H, 2 s) 1.58 and 1.68 (3H, 2 s) 2.28-3.02 (4H, m) 4.01-4.15 (2H, m) 4.94 and 5.11 (1H, 2 d, J=12 Hz) 5.10 and 5.16 (1H, 2 d, J=12 Hz) 7.28-7.40 (5H, m).

(Step 4)

4-(3-Benzyloxycarbonyl-2,2-dimethyl-5R-methyloxazolidin-4S-yl)-4-oxobutyric acid methyl ester (compound 4)

The compound 3 (5.2 g, 15 mmol) was dissolved in toluene (240 ml). To the solution, MeOH (60 ml) and trimethylsilyldiazomethane (10% hexane solution, 27 ml) were added, and the mixture was stirred at room temperature for 1 hour. To the reaction mixture, acetic acid was added dropwise. The disappearance of the yellow color was confirmed, and the solvent was then distilled off under reduced pressure. The residue was purified by silica gel column chromatography (hexane:AcOEt=8:1) to obtain the title compound (4.6 g, 12.7 mmol, 85%).

$^1$H-NMR (CDCl$_3$) δ: 1.41 and 1.42 (3H, 2 d, J=6 Hz) 1.57 and 1.63 (3H, 2 s) 1.58 and 1.68 (3H, 2 s) 2.20-3.00 (4H, m) 3.64 and 3.70 (3H, 2 s) 3.97-4.18 (2H, m) 4.94 and 5.10 (1H, 2 d, J=12 Hz) 5.10 and 5.15 (1H, 2 d, J=12 Hz) 7.26-7.38 (5H, m).

(Step 5)

3-Benzyloxycarbonyl-2,2-dimethyl-5R-methyl-4S-[5-oxotetrahydrofuran-2-yl]oxazolidine (compound 5)

The compound 4 (4.13 g, 11.4 mmol) was dissolved in MeOH (120 ml). To the solution, NaBH$_4$ (860 mg, 23 mmol) was added, and the mixture was stirred at room temperature for 3 hours. From the reaction mixture, the solvent was distilled off under reduced pressure. Then, to the residue, water was added, followed by extraction with chloroform. The organic layer was dried over anhydrous magnesium sulfate, and the solvent was distilled off under reduced pressure. The obtained residue was dissolved in toluene (100 ml). To the solution, acetic acid (3 ml) was added, and the mixture was stirred for 4 hours under reflux. To the reaction mixture, an aqueous solution of saturated sodium bicarbonate was added, followed by extraction with chloroform. The organic layer was dried over anhydrous magnesium sulfate, and the solvent was distilled off under reduced pressure. Then, the residue was purified by silica gel column chromatography (hexane: AcOEt=3:1 to 2:1) to obtain the title compound (2.99 g, 9.00 mmol, 79%).

$^1$H-NMR (CDCl$_3$) δ: 1.39 (3H, d, J=6 Hz) 1.53 (3H, s) 1.59 (3H, s) 1.95-2.23 (2H, m) 2.42-2.57 (2H, m) 3.98-4.16 (2H, m) 4.79 and 5.06 (1H, 2 m) 5.15 (2H, s) 7.28-7.40 (5H, m).

(Step 6)

3-Benzyloxycarbonyl-2,2-dimethyl-5R-methyl-4S-[4R-(2-methyl-2-propenyl)-5-oxotetrahydrofuran-2S-yl]oxazolidine (compound 6)

The compound 5 (2.99 g, 9.0 mmol) was dissolved in THF (50 ml) in an argon atmosphere, and the solution was stirred at −78° C. for 20 minutes. Then, LiHMDS (1.0 M THF solution, 12 ml, 12 mmol) was added thereto, and the mixture was stirred at −78° C. for 1 hour. To the reaction system, 3-bromo-2-methylpropene (1.2 ml, 12 mmol) was added dropwise using a syringe, and the mixture was further stirred at −78° C. for 2 hours. To the reaction mixture, an aqueous citric acid solution was added, followed by extraction with chloroform. The organic layer was dried over anhydrous magnesium sulfate, and the solvent was distilled off under reduced pressure. Then, the residue was purified by silica gel column chromatography (hexane:AcOEt=4:1 to 3:1) to obtain the title compound (2.22 g, 5.7 mmol, 83%).

$^1$H-NMR (CDCl$_3$) δ: 1.37 (3H, d, J=6 Hz) 1.55 (3H, m) 1.60 (3H, s) 1.69 (3H, s) 1.95 (1H, m) 2.09 (1H, m) 2.30 (1H, m) 2.53 (1H, m) 2.65 and 2.79 (1H, 2 m) 3.90-4.13 (2H, m) 4.68 (1H, m) 4.81 (1H, m) 5.11 (1H, m) 5.15 and 5.18 (2H, 2 s) 7.30-7.40 (5H, m).

(Step 7)

2R-Hydroxy-1S-[4R-(2-methylpropyl)-5-oxotetrahydrofuran-2S-yl]propylcarbamic acid tert-butyl ester (compound 7)

The compound 6 (1.30 g, 3.36 mmol) was dissolved in methanol (120 ml) and 0.1 N hydrochloric acid (30 ml). To the solution, 10% palladium-carbon (0.9 g) was added with stirring. The atmosphere in the reaction system was replaced with hydrogen using a balloon filled with hydrogen gas, and the reaction mixture was stirred overnight at room temperature. The reaction mixture was filtered through a celite pad, and the filtrate was concentrated. The residue was dissolved in ethyl acetate (300 ml). To the solution, water (90 ml) and sodium bicarbonate (1.68 g, 20 mmol) were added, and the mixture was stirred for 10 minutes in an ice bath. To the reaction system, Boc$_2$O (800 mg, 3.67 mmol) was gradually added dropwise, and the mixture was stirred for 6 hours in an ice bath and further stirred overnight at room temperature. To the reaction mixture, chloroform was added, and the organic layer was washed with an aqueous solution of saturated sodium bicarbonate. The organic layer was dried over anhydrous magnesium sulfate, and the solvent was distilled off under reduced pressure. Then, the residue was purified by silica gel column chromatography (hexane:AcOEt=4:1 to 2:1) to obtain the title compound (0.62 g, 1.97 mmol, 59% in 2 steps).

$^1$H-NMR (CDCl$_3$) δ: 0.90 (3H, d, J=7 Hz) 0.95 (3H, d, J=6 Hz) 1.22 (3H, d, J=6 Hz) 1.34 (1H, m) 1.45 (9H, s) 1.62-1.73 (2H, m) 1.98 (1H, m) 2.43 (1H, m) 2.68 (1H, m) 3.62 (1H, m) 4.13 (1H, m) 4.70 (1H, m) 5.05 (1H, d, J=9 Hz, NH).

(Step 8)

2R-(tert-Butyldimethylsilyloxy)-1S-[4R-(2-methylpropyl)-5-oxotetrahydrofuran-2S-yl]propyl carbamic acid tert-butyl ester (compound 8)

The compound 7 (0.62 g, 1.97 mmol) was dissolved in DMF (100 ml). To the solution, imidazole (2.7 g, 40 mmol), DMAP (24 mg, 0.2 mmol), and t-butyldimethylchlorosilane (3.0 g, 20 mmol) were added, and the mixture was stirred at 50° C. for 5 hours. The reaction mixture was cooled to room temperature. Methanol was added thereto, and the mixture was stirred for 0.5 hours. The solvent was distilled off under reduced pressure. Then, to the reaction mixture, chloroform was added, and the organic layer was washed with an aqueous citric acid solution and saturated saline. The organic layer was dried over anhydrous magnesium sulfate, and the solvent was distilled off under reduced pressure. Then, the residue was purified by silica gel column chromatography (hexane:AcOEt=8:1) to obtain the title compound (0.81 g, 1.89 mmol, 96%).

$^1$H-NMR (CDCl$_3$) δ: 0.07 (3H, s) 0.08 (3H, s) 0.88 (9H, s) 0.89 (3H, d, J=6 Hz) 0.94 (3H, d, J=7 Hz) 1.19 (3H, d, J=6 Hz) 1.31 (1H, m) 1.43 (9H, s) 1.61-1.71 (2H, m) 1.96 (1H, m) 2.31 (1H, m) 2.65 (1H, m) 3.60 (1H, m) 3.90 (1H, m) 4.63 (1H, m) 4.66 (1H, d, J=10 Hz, NH).

(Step 9)

[5S-(tert-Butoxycarbonylamino)-6R-(tert-butyldimethylsilyloxy)-4S-hydroxy-2R-(2-methylpropyl)heptyl]acetate (compound 9)

The compound 8 (0.81 g, 1.89 mmol) was dissolved in THF (11 ml) and ethanol (11 ml). To the solution, calcium chloride (420 mg, 3.8 mmol) was added, and the mixture was stirred for 15 minutes in an ice bath. Then, NaBH$_4$ (290 mg, 7.6 mmol) was added thereto, and the mixture was stirred for 3 hours in an ice bath. While the reaction mixture was cooled in an ice bath, a 1 M aqueous KHSO$_4$ solution was added thereto. The mixture was stirred for 15 minutes, followed by extraction with ethyl acetate. The organic layer was washed with an aqueous solution of saturated sodium bicarbonate and then dried over anhydrous magnesium sulfate. The solvent was distilled off under reduced pressure to obtain a diol form (0.85 g). The diol form (0.85 g) was dissolved in methylene chloride (50 ml) in an argon atmosphere, and the solution was stirred for 10 minutes in an ice bath. Then, triethylamine (273 mg, 2.7 mmol) and acetyl chloride (212 mg, 2.7 mmol) were added thereto, and the mixture was stirred for 3 hours in an ice bath. To the reaction mixture, methanol (1 ml) was added, and the mixture was stirred for 10 minutes, and the solvent was then distilled off. The residue was purified by silica gel column chromatography (hexane:AcOEt=8:1 to 6:1) to obtain the title compound (0.66 g, 1.39 mmol, 73% in 2 steps).

$^1$H-NMR (CDCl$_3$) δ: 0.11 (3H, S) 0.12 (3H, S) 0.87 (3H, d, J=7 Hz) 0.88 (3H, d, J=7 Hz) 0.89 (9H, S) 1.12 (1H, m) 1.18 (3H, d, J=6 Hz) 1.25 (1H, m) 1.37 (1H, m) 1.45 (9H, s) 1.47 (1H, m) 1.62 (1H, m) 1.98 (1H, m) 2.04 (3H, S) 3.35 (1H, m) 3.91 (1H, m) 3.97-4.10 (2H, m) 4.12 (1H, m) 5.09 (1H, d, J=10 Hz, NH).
(Step 10)

[4S, 6R-Bis(tert-butyldimethylsilyloxy)-5S-(tert-butoxycarbonylamino)-2R-(2-methylpropyl)heptyl] acetate (compound 10)

The compound 9 (0.66 g, 1.39 mmol) was dissolved in methylene chloride (20 ml) in an argon atmosphere. To the solution, 2,6-lutidine (500 mg, 4.7 mmol) and t-butyldimethylsilyl trifluoromethanesulfonate (0.53 ml, 2.3 mmol) were added, and the mixture was stirred at room temperature for 3 hours. To the reaction mixture, saturated saline was added, followed by extraction with chloroform. The organic layer was dried over anhydrous magnesium sulfate, and the solvent was distilled off under reduced pressure. Then, the residue was purified by silica gel column chromatography (hexane:AcOEt=9:1) to obtain the title compound (0.55 g, 0.93 mmol, 67%).

$^1$H-NMR (CDCl$_3$) δ: 0.07 (3H, S) 0.08 (3H, S) 0.08 (3H, S) 0.10 (3H, S) 0.87 (3H, d, J=6 Hz) 0.88 (3H, d, J=6 Hz) 0.89 (9H, S) 0.89 (9H, S) 1.05 (1H, m) 1.16 (3H, d, J=6 Hz) 1.22 (1H, m) 1.37 (1H, m) 1.44 (9H, s) 1.54 (1H, m) 1.61 (1H, m) 1.81 (1H, m) 2.04 (3H, S) 3.42 (1H, m) 3.89 (1H, m) 3.90-4.00 (2H, m) 4.90 (1H, m) 4.81 (1H, d, J=10 Hz, NH).
(Step 11)

1S-(1R-tert-Butyldimethylsilyloxyethyl)-2S-(tert-butyldimethylsilyloxy)-4R-hydroxymethyl-6-methylheptyl carbamic acid tert-butyl ester (compound 11)

The compound 10 (0.10 g, 0.17 mmol) was dissolved in THF (4 ml) and ethanol (4 ml). To the solution, calcium chloride (114 mg, 1.0 mmol) was added, and the mixture was stirred for 15 minutes in an ice bath. Then, NaBH$_4$ (78 mg, 2.0 mmol) was added thereto, and the mixture was stirred for 1 hour in an ice bath and further stirred at room temperature for 24 hours. While the reaction mixture was cooled in an ice bath, a 1 M aqueous KHSO$_4$ solution was added thereto. The mixture was stirred for 15 minutes, followed by extraction with ethyl acetate. The organic layer was washed with an aqueous solution of saturated sodium bicarbonate and then dried over anhydrous magnesium sulfate, and the solvent was distilled off under reduced pressure. The residue was purified by silica gel column chromatography (hexane:AcOEt=8:1) to obtain the title compound (0.09 g, 0.16 mmol, 97%).

$^1$H-NMR (CDCl$_3$) δ: 0.06 (3H, S) 0.07 (3H, S) 0.08 (3H, S) 0.09 (3H, S) 0.88 (3H, d, J=6 Hz) 0.89 (9H, s) 0.89 (3H, d, J=6 Hz) 0.90 (9H, S) 1.04 (1H, m) 1.15 (1H, m) 1.18 (3H, d, J=6 Hz) 1.27 (1H, m) 1.44 (9H, s) 1.56-1.68 (3H, m) 1.78 (1H, m) 3.26 (1H, m) 3.53-3.64 (2H, m) 3.31-3.41 (2H, m) 4.70 (1H, d, J=10 Hz, NH).
(Step 12)

4S, 6R-Bis(tert-butyldimethylsilyloxy)-5S-(tert-butoxycarbonylamino)-2R-(2-methylpropyl)heptanoic acid (compound 12)

The compound 11 (0.36 g, 0.66 mmol) was dissolved in acetonitrile (4 ml) and carbon tetrachloride (4 ml). To the solution, water (6 ml) and sodium periodate (0.55 g, 2.56 mmol) were added, and the mixture was stirred at room temperature for 5 minutes. Then, ruthenium chloride.nH$_2$O (20 mg) was added thereto, and further, the mixture was vigorously stirred at room temperature for 3 hours. To the reaction mixture, water and chloroform were added. The organic layer was separated and then filtered through a celite pad, and the filtrate was washed with saturated saline. The organic layer was dried over anhydrous magnesium sulfate, and the solvent was distilled off under reduced pressure to obtain the title compound (0.37 g). This compound was directly used in the next reaction.
(Step 13)

4S, 6R-Bis(tert-butyldimethylsilyloxy)-5S-(tert-butoxycarbonylamino)-2R-(2-methylpropyl)heptanoic acid 1S-hydroxymethyl-2-methylpropylamide (compound 13)

The compound 12 (0.37 g) and L-valinol (83 mg, 0.80 mmol) were dissolved in DMF (30 ml), and the solution was stirred for 10 minutes in an ice bath. Then, diethyl cyanophosphonate (DEPC, 130 mg, 0.830 mmol) and diisopropylethylamine (103 mg, 0.80 mmol) were added thereto, and the mixture was stirred for 1 hour in an ice bath and further stirred overnight at room temperature. To the reaction mixture, ethyl acetate was added, and the organic layer was washed with an aqueous potassium bisulfate solution, water, and an aqueous solution of saturated sodium bicarbonate in this order. The organic layer was dried over anhydrous magnesium sulfate, and the solvent was distilled off under reduced pressure. Then, the residue was purified by silica gel column chromatography (CHCl$_3$:MeOH=98:2) to obtain the title compound (0.39 g, 0.60 mmol, 91% in 2 steps).

$^1$H-NMR (CDCl$_3$) δ: 0.05 (3H, s) 0.06 (3H, s) 0.08 (3H, s) 0.10 (3H, s) 0.89 (9H, s) 0.89 (9H, s) 0.89 (3H, d, J=6 Hz) 0.90 (3H, d, J=6 Hz) 0.93 (3H, d, J=7 Hz) 0.95 (3H, d, J=7 Hz) 1.07 (1H, m) 1.18 (3H, d, J=6 Hz) 1.40 (9H, s) 1.54 (1H, m) 1.72 (1H, m) 1.76 (1H, m) 1.98 (1H, m) 2.40 (1H, m) 3.41 (1H, m) 3.42 (1H, m) 3.64 (1H, m) 3.72 (1H, m) 3.78-3.88 (2H, m) 4.72 (1H, d, J=10 Hz, NH) 6.45 (1H, m, NH).
(Step 14)

[4S, 6R-Bis(tert-butyldimethylsilyloxy)-5S-(tert-butoxycarbonylamino)-2R-(2-methylpropyl)heptanoyl]-L-valine (compound 14)

The compound 13 (0.39 g, 0.60 mmol) was dissolved in acetonitrile (3.2 ml) and carbon tetrachloride (3.2 ml). To the solution, water (4.8 ml) and sodium periodate (496 mg, 2.32 mmol) were added, and the mixture was stirred at room temperature for 5 minutes. Then, ruthenium chloride.nH₂O (4 mg) was added thereto, and further, the mixture was vigorously stirred at room temperature for 3 hours. To the reaction mixture, water and chloroform were added. The organic layer was separated and then filtered through a celite pad, and the filtrate was washed with saturated saline. The organic layer was dried over anhydrous magnesium sulfate, and the solvent was distilled off under reduced pressure to obtain the title compound (0.33 g, 83%). This compound was directly used in the next reaction.

$^1$H-NMR (CDCl$_3$) δ: 0.03 (3H, s) 0.05 (3H, s) 0.08 (3H, s) 0.11 (3H, s) 0.81 (3H, d, J=6 Hz) 0.84 (3H, d, J=6 Hz) 0.85 (9H, s) 0.86 (3H, d, J=7 Hz) 0.87 (9H, s) 0.88 (3H, d, J=7 Hz) 1.05 (1H, m) 1.13 (3H, d, J=6 Hz) 1.38 (9H, s) 1.40-1.56 (2H, m) 1.67-1.80 (2H, m) 2.23 (1H, m) 2.40 (1H, m) 3.56 (1H, m) 3.72-3.82 (2H, m) 4.51 (1H, m) 4.94 (1H, d, J=10 Hz, NH) 7.33 (1H, d, J=7 Hz, NH).

(Step 15)

[4S,6R-Bis(tert-butyldimethylsilyloxy)-5S-(tert-butoxycarbonylamino)-2R-(2-methylpropyl)heptanoyl]-L-valyl-L-methionine benzylamide (compound 15)

The compound 14 (0.18 g, 0.27 mmol) and H-Met-NHBn were dissolved in THF (4 ml) in an argon atmosphere. To the solution, 4-(4,6-dimethoxy-1,3,5-triazin-2-yl)-4-methyl morpholinium chloride (DMT-MM nH₂O, 125 mg) was added with stirring, and the mixture was stirred overnight at room temperature. To the reaction mixture, ethyl acetate was added, and the organic layer was washed with an aqueous potassium bisulfate solution and saturated saline in this order. The organic layer was dried over anhydrous magnesium sulfate, and the solvent was distilled off under reduced pressure. Then, the residue was purified by silica gel column chromatography (CHCl$_3$:MeOH=98:2) to obtain the title compound (0.14 g, 0.15 mmol, 67%).

$^1$H-NMR (CDCl$_3$) δ: 0.06 (3H, s) 0.07 (3H, s) 0.08 (3H, s) 0.10 (3H, s) 0.84 (3H, d, J=7 Hz) 0.88 (3H, d, J=7 Hz) 0.89 (9H, s) 0.89 (9H, s) 0.90 (3H, d, J=7 Hz) 0.94 (3H, d, J=7 Hz) 1.07 (1H, m) 1.18 (3H, d, J=6 Hz) 1.43 (9H, s) 1.48 (1H, m) 1.63 (1H, m) 1.69-1.82 (2H, m) 1.94 (1H, m) 2.05-2.11 (2H, m) 2.06 (3H, s) 2.40 (1H, m) 2.44-2.59 (2H, m) 3.44 (1H, m) 3.78 (1H, m) 3.90 (1H, m) 4.05 (1H, m) 4.37-4.48 (2H, m) 4.58 (1H, m) 4.70 (1H, d, J=10 Hz, NH) 6.46 (1H, br d, J=7 Hz, NH) 6.64 (1H, br d, J=8 Hz, NH) 6.86 (1H, m, NH) 7.20-7.35 (5H, m).

(Step 16)

[5S-(tert-Butoxycarbonylamino)-4S,6R-dihydroxy-2R-(2-methylpropyl)heptanoyl]-L-valyl-L-methionine benzylamide (TLVM-4)

The compound 15 (0.15 g, 0.17 mmol) was dissolved in THF (3 ml). To the solution, acetic acid (80 mg) was added. Then, tetrabutylammonium fluoride.nH₂O (TBAF, 0.47 g) was added thereto, and the mixture was stirred at room temperature for 8 days. To the reaction mixture, chloroform was added, and the crude product was purified by silica gel column chromatography (CHCl$_3$:MeOH=97:3) to obtain the title compound (0.06 g, 0.092 mmol, 81%).

$^1$H-NMR (CDCl$_3$-CD$_3$OD) δ: 0.86 (3H, d, J=7 Hz) 0.89 (3H, d, J=7 Hz) 0.90 (3H, d, J=7 Hz) 0.92 (3H, d, J=7 Hz) 1.15 (3H, d, J=6 Hz) 1.21 (1H, m) 1.44 (9H, s) 1.46 (1H, m) 1.53-1.64 (2H, m) 1.66 (1H, m) 1.94 (1H, m) 2.00-2.15 (2H, m) 2.07 (3H, s) 2.42-2.50 (2H, m) 2.60 (1H, m) 3.38 (1H, m) 3.77 (1H, m) 4.02 (1H, m) 4.10 (1H, m) 4.37 (1H, d, J=15 Hz) 4.42 (1H, d, J=15 Hz) 4.50 (1H, m) 7.20-7.37 (5H, m).

Example 2

Production of [5S-(tert-butoxycarbonylamino)-4R,6R-dihydroxy-2R-(2-methylpropyl)heptanoyl]-L-valyl-L-methionine benzylamide (TLVM-5)

(Step 1)

1S-[4R-(2-Methylpropyl)-5-oxotetrahydrofuran-2S-yl]-2R-triethylsilyloxy-propyl carbamic acid tert-butyl ester (compound 16)

The title compound (1.73 g, 4.0 mmol, 85%) was obtained from the compound 7 (2.00 g, 6.3 mmol) and triethylsilyl trifluoromethanesulfonate (2.64 g, 10 mmol) in the same way as in the synthesis of the compound 10.

$^1$H-NMR (CDCl$_3$) δ: 0.56-0.65 (6H, m) 0.89 (3H, d, J=6 Hz) 0.92-1.00 (9H, m) 0.96 (3H, d, J=6 Hz) 1.20 (3H, d, J=6 Hz) 1.33 (1H, m) 1.44 (9H, s) 1.64-1.73 (2H, m) 1.96 (1H, m) 1.96 (1H, m) 2.30 (1H, m) 2.65 (1H, m) 3.61 (1H, m) 3.92 (1H, m) 4.66 (1H, m) 4.74 (1H, d, J=10 Hz, NH).

(Step 2)

[5S-(tert-Butoxycarbonylamino)-4S-hydroxy-2R-(2-methylpropyl)-6R-triethylsilyloxyheptyl]acetate (compound 17)

The title compound (1.73 g, 3.6 mmol, 91% in 2 steps) was obtained from the compound 16 (1.73 g, 4.0 mmol) in the same way as in the synthesis of the compound 9.

$^1$H-NMR (CDCl$_3$) δ: 0.65 (2H×3, q, J=8 Hz) 0.89 (3H, d, J=7 Hz) 0.89 (3H, d, J=7 Hz) 0.98 (3H×3, t, J=8 Hz) 1.14 (1H, m) 1.21 (3H, d, J=6 Hz) 1.27 (1H, m) 1.38 (1H, m) 1.47 (9H, s) 1.50 (1H, m) 1.65 (1H, m) 1.98 (1H, m) 2.05 (3H, s) 3.36 (1H, m) 3.42 (1H, br s, OH) 3.97 (1H, m) 4.00-4.14 (2H, m) 4.18 (1H, m) 5.15 (1H, d, J=10 Hz, NH).

(Step 3)

[5S-(tert-Butoxycarbonylamino)-2R-(2-methylpropyl)-4-oxo-6R-triethylsilyloxyheptyl]acetate (compound 18)

The compound 17 (1.73 g, 3.6 mmol) was dissolved in methylene chloride (20 ml). To the solution, a Dess-Martin reagent (DMP, 1.7 g, 4.0 mmol) was added. Then, to the mixture, water-saturated methylene chloride (2 ml) was gradually added, and the mixture was stirred at room temperature for 3 hours. To the reaction mixture, an aqueous sodium thiosulfate solution was added, followed by extraction with chloroform. The organic layer was dried over anhydrous magnesium sulfate, and the solvent was distilled off under reduced pressure. Then, the residue was purified by silica gel column chromatography (hexane:AcOEt=9:1) to obtain the title compound (1.44 g, 3.0 mmol, 84%).

$^1$H-NMR (CDCl$_3$) δ: 0.58 (2H×3, q, J=8 Hz) 0.86 (3H, d, J=7 Hz) 0.91 (3H, d, J=7 Hz) 0.93 (3H×3, t, J=8 Hz) 1.11 (1H, m) 1.13 (3H, d, J=6 Hz) 1.18 (1H, m) 1.46 (9H, s) 1.58 (1H, m) 2.02 (3H, s) 2.36 (1H, m) 2.41 (1H, dd, J=18, 6 Hz) 2.74 (1H, dd, J=18, 6 Hz) 3.92 (1H, dd, J=11, 6 Hz) 4.03 (1H, dd, J=11, 5 Hz) 4.12 (1H, dd, J=9, 3 Hz) 4.36 (1H, dq, J=6, 3 Hz) 5.37 (1H, d, J=9 Hz, NH).

(Step 4)

[5S-(tert-Butoxycarbonylamino)-6R-hydroxy-2R-(2-methylpropyl)-4-oxoheptyl]acetate (compound 19)

The compound 18 (0.25 g, 0.53 mmol) was dissolved in THF (4 ml). To the solution, water (1 ml) and acetic acid (4 ml) were added, and the mixture was stirred at room temperature for 5 hours. To the reaction mixture, an aqueous solution of saturated sodium bicarbonate was carefully added. Gas was completely generated, followed by extraction with chloroform. The organic layer was dried over anhydrous magnesium sulfate, and the solvent was distilled off under reduced pressure to obtain the title compound (0.24 g).

$^1$H-NMR (CDCl$_3$) δ: 0.87 (3H, d, J=6 Hz) 0.91 (3H, d, J=6 Hz) 1.10 (1H, m) 1.21 (3H, d, J=7 Hz) 1.22 (1H, m) 1.45 (9H, s) 1.59 (1H, m) 2.03 (3H, s) 2.38 (1H, m) 2.50 (1H, dd, J=18, 5 Hz) 2.65 (1H, dd, J=18, 8 Hz) 3.87 (1H, dd, J=11, 6 Hz) 4.14 (1H, dd, J=11, 4 Hz) 4.19 (1H, br d, J=9 Hz) 4.30 (1H, m) 5.41 (1H, d, J=9 Hz, NH).

(Step 5)

2R-[5S-(tert-Butoxycarbonylamino)-2,2-dimethyl-6R-methyl-1,3-dioxan-4R-yl]methyl-4-methylpentyl acetate (compound 20)

The compound 19 (0.24 g) was dissolved in THF (5 ml), and the solution was stirred for 10 minutes in an ice bath. Then, a suspension of NaBH(OAc)$_3$ (318 mg, 1.5 mmol) in THF (3 ml) and acetic acid (0.3 ml) was added thereto, and the mixture was stirred for 1 hour in an ice bath and further stirred at room temperature for 3 hours. To the reaction mixture, an aqueous potassium acetate solution was added, and the mixture was stirred for 10 minutes. Then, saturated saline was added thereto, followed by extraction with chloroform. The organic layer was dried over anhydrous magnesium sulfate, and the solvent was distilled off under reduced pressure. The residue was dissolved in toluene (30 ml). To the solution, 2-methoxypropene (1.2 ml) and PPTS (30 mg) were added, and the mixture was stirred at 70° C. for 3 hours. The toluene was distilled off. Then, to the residue, chloroform was added, and the organic layer was washed with an aqueous solution of saturated sodium bicarbonate. The organic layer was dried over anhydrous magnesium sulfate, and the solvent was distilled off under reduced pressure. Then, the residue was purified by silica gel column chromatography (hexane:AcOEt=9:1 to 6:1) to obtain the title compound (0.09 g, 0.22 mmol, 42% in 3 steps) and a protected 5-membered cyclic form (0.08 g).

$^1$H-NMR (CDCl$_3$) δ: 0.86 (3H, d, J=7 Hz) 0.88 (3H, d, J=7 Hz) 1.09 (3H, d, J=6 Hz) 1.11 (1H, m) 1.15 (1H, m) 1.32 (3H, s) 1.44 (9H, s) 1.56 (3H, s) 1.56 (1H, m) 1.60-1.73 (2H, m) 1.91 (1H, m) 2.05 (3H, s) 3.35 (1H, ddd, J=10, 7, 3 Hz) 3.57 (1H, ddd, J=10, 8, 5 Hz) 3.94-4.04 (2H, m) 4.08 (1H, m) 4.65 (1H, d, J=10 Hz, NH).

(Step 6)

[2,2-Dimethyl-4R-(2R-hydroxymethyl-4-methylpentyl)-6R-methyl-1,3-dioxan-5S-yl]carbamic acid tert-butyl ester (compound 21)

The title compound (0.12 g) was obtained from the compound 20 (0.12 g, 0.30 mmol) in the same way as in the synthesis of the compound 11. This compound was directly used in the next reaction.

(Step 7)

2R-[5S-(tert-Butoxycarbonylamino)-2,2-dimethyl-6R-methyl-1,3-dioxan-4R-yl]methyl-4-methylpentanoic acid (compound 22)

The title compound (0.38 g, 1.0 mmol, 95% in 2 steps) was obtained from the compound 21 (0.43 g) in the same way as in the synthesis of the compound 12.

$^1$H-NMR (CDCl$_3$) δ: 0.89 (3H, d, J=6 Hz) 0.90 (3H, d, J=6 Hz) 1.09 (3H, d, J=6 Hz) 1.25 (1H, m) 1.30 (3H, s) 1.43 (9H, s) 1.46 (3H, s) 1.55-1.65 (2H, m) 1.77 (1H, m) 1.96 (1H, m) 2.52 (1H, m) 3.35 (1H, m) 4.08 (1H, m) 4.80 (1H, d, J=10 Hz, NH).

(Step 8)

2R-[5S-(tert-Butoxycarbonylamino)-2,2-dimethyl-6R-methyl-1,3-dioxan-4R-yl]methyl-4-methylpentanoyl-L-valyl-L-methionine benzylamide (compound 23)

The title compound (0.10 g, 0.14 mmol, 48%) was obtained from the compound 22 (0.11 g, 0.29 mmol) and H-Val-Met-NHBn in the same way as in the synthesis of the compound 15.

$^1$H-NMR (CDCl$_3$) δ: 0.85 (3H, d, J=7 Hz) 0.86 (3H, d, J=7 Hz) 0.91 (3H, d, J=7 Hz) 0.93 (3H, d, J=7 Hz) 1.09 (3H, d, J=7 Hz) 1.21 (1H, m) 1.32 (3H, s) 1.44 (9H, s) 1.46 (3H, s) 1.58 (1H, m) 1.73-1.90 (2H, m) 1.92-2.17 (4H, m) 2.05 (3H, s) 2.39 (1H, m) 2.41-2.59 (2H, m) 3.34 (1H, m) 3.56 (1H, m) 4.05 (1H, m) 4.18 (1H, m) 4.42 (1H, d, J=6 Hz) 4.43 (1H, d, J=6 Hz) 4.55 (1H, m) 4.61 (1H, d, J=7 Hz, NH) 6.28 (1H, m, NH) 6.78 (1H, m, NH) 6.84 (1H, m, NH) 7.20-7.34 (5H, m).

(Step 9)

[5S-(tert-Butoxycarbonylamino)-4R,6R-dihydroxy-2R-(2-methylpropyl)heptanoyl]-L-valyl-L-methionine benzylamide (TLVM-5)

The compound 23 (0.10 g, 0.14 mmol) was dissolved in methanol (20 ml). To the solution, PPTS (20 mg) was added, and the mixture was then stirred at 40° C. for 24 hours. The methanol was distilled off under reduced pressure. Then, the residue was purified by silica gel column chromatography (CHCl$_3$:MeOH=98:2) to obtain the title compound (0.07 g, 0.107 mmol, 77%).

$^1$H-NMR (CDCl$_3$-CD$_3$OD) δ: 0.87 (3H, d, J=6 Hz) 0.91 (3H, d, J=7 Hz) 0.91 (3H, d, J=6 Hz) 0.93 (3H, d, J=7 Hz) 1.15 (3H, d, J=6 Hz) 1.24 (1H, m) 1.45 (9H, s) 1.46-1.61 (2H, m) 1.66-1.81 (2H, m) 1.94 (1H, m) 2.03-2.16 (2H, m) 2.08 (3H, s) 2.44-2.55 (3H, m) 3.28 (1H, m) 3.64 (1H, m) 4.11 (1H, d, J=7 Hz) 4.23 (1H, m) 4.32-4.43 (2H, m) 4.50 (1H, m) 7.22-7.35 (5H, m).

Example 3

Production of [5S-(tert-butoxycarbonylamino)-4R,6R-dihydroxy-2R-(2-methylpropyl)heptanoyl]-L-valyl-L-methionine n-butylamide (TLVM-7)

(Step 1)

2R-[5S-(tert-Butoxycarbonylamino)-2,2-dimethyl-6R-methyl-1,3-dioxan-4R-yl]methyl-4-methylpentanoyl-L-valyl-L-methionine n-butylamide (compound 24)

The title compound (0.17 g) was obtained from the compound 22 (0.08 g, 0.21 mmol) and H-Val-Met-NH-n-Pr in the same way as in the synthesis of the compound 15.

¹H-NMR (CDCl₃) δ: 0.88 (3H, d, J=7 Hz) 0.90 (3H, d, J=7 Hz) 0.91 (3H, t, J=6 Hz) 0.96 (3H, d, J=7 Hz) 1.01 (3H, d, J=7 Hz) 1.09 (3H, d, J=6 Hz) 1.20 (1H, m) 1.31 (2H, m) 1.33 (3H, s) 1.34 (3H, s) 1.44 (9H, s) 1.46 (2H, m) 1.62 (1H, m) 1.75-1.89 (2H, m) 1.90-2.14 (4H, m) 2.09 (3H, s) 2.26 (1H, m) 2.43-2.61 (2H, m) 3.22 (2H, m) 3.35 (1H, m) 3.57 (1H, m) 4.05 (1H, m) 4.17 (1H, m) 4.40 (1H, m) 4.72 (1H, d, J=10 Hz, NH) 6.25 (1H, br d, J=9 Hz, NH) 6.77 (1H, br d, J=9 Hz, NH) 7.25 (1H, br d, J=10 Hz, NH).
(Step 2)

[5S-(tert-Butoxycarbonylamino)-4R,6R-dihydroxy-2R-(2-methylpropyl)heptanoyl]-L-valyl-L-methionine n-butylamide (TLVM-7)

The title compound (0.07 g, 0.11 mmol, 54% in 2 steps) was obtained from the compound 24 (0.16 g) in the same way as in the synthesis of the TLVM-5.

¹H-NMR (CDCl₃-CD₃OD) δ: 0.88 (3H, d, J=6 Hz) 0.91 (3H, d, J=7 Hz) 0.92 (3H, t, J=7 Hz) 0.92 (3H, d, J=7 Hz) 0.93 (3H, d, J=7 Hz) 1.18 (3H, d, J=6 Hz) 1.29 (1H, m) 1.34 (2H, m) 1.40-1.61 (3H, m) 1.44 (9H, s) 1.77-1.86 (2H, m) 1.97 (1H, m) 2.02-2.13 (2H, m) 2.09 (3H, s) 2.31 (1H, m) 2.43-2.59 (3H, m) 3.12-3.35 (3H, m) 3.75 (1H, m) 4.20 (1H, m) 4.32 (1H, m) 4.60 (1H, m) 5.34 (1H, d, J=8 Hz, NH) 6.70 (1H, m, NH) 6.92 (1H, m, NH) 7.92 (1H, m, NH).

Example 4

Production of [5S-(tert-butoxycarbonylamino)-4R,6R-dihydroxy-2R-(2-methylpropyl)heptanoyl]-L-valyl-L-methionine (S)-α-methylbenzylamide (TLVM-8)

(Step 1)

2R-[5S-(tert-Butoxycarbonylamino)-2,2-dimethyl-6R-methyl-1,3-dioxan-4R-yl]methyl-4-methylpentanoyl-L-valyl-L-methionine (S)-α-methylbenzylamide (compound 25)

The title compound (0.12 g) was obtained from the compound 22 (0.07 g, 0.19 mmol) and H-Val-Met-NH—(S)—CH(Me)Ph in the same way as in the synthesis of the compound 15.

¹H-NMR (CDCl₃) δ: 0.88 (3H, d, J=6 Hz) 0.90 (3H, d, J=7 Hz) 0.92 (3H, d, J=6 Hz) 0.96 (3H, d, J=7 Hz) 1.09 (3H, d, J=7 Hz) 1.26 (1H, m) 1.33 (3H, d, J=7 Hz) 1.44 (9H, s) 1.45 (3H, s) 1.48 (3H, s) 1.59 (1H, m) 1.79 (1H, m) 1.83-2.22 (4H, m) 2.01 (3H, s) 2.26-2.60 (4H, m) 3.36 (1H, m) 3.57 (1H, m) 4.06 (1H, m) 4.21 (1H, m) 4.56 (1H, m) 4.72 (1H, d, J=10 Hz, NH) 5.07 (1H, m) 6.23 (1H, m, NH) 6.69 (1H, m, NH) 6.76 (1H, m, NH) 7.21-7.36 (5H, m).
(Step 2)

[5S-(tert-Butoxycarbonylamino)-4R,6R-dihydroxy-2R-(2-methylpropyl)heptanoyl]-L-valyl-L-methionine (S)-α-methylbenzylamide (TLVM-8)

The title compound (0.08 g, 0.12 mmol, 63% in 2 steps) was obtained from the compound 25 (0.12 g) in the same way as in the synthesis of the TLVM-5.

¹H-NMR (CDCl₃-CD₃OD) δ: 0.88 (3H, d, J=6 Hz) 0.92 (3H, d, J=7 Hz) 0.92 (3H, d, J=7 Hz) 0.94 (3H, d, J=7 Hz) 1.15 (3H, d, J=6 Hz) 1.27 (1H, m) 1.44 (9H, s) 1.46 (3H, d, J=7 Hz) 1.47-1.58 (2H, m) 1.72-1.81 (2H, m) 1.88 (1H, m) 1.96-2.06 (2H, m) 2.02 (3H, s) 2.24 (1H, m) 2.31-2.44 (3H, m) 2.50 (1H, m) 3.28 (1H, m) 3.68 (1H, m) 4.18 (1H, d, J=7 Hz) 4.26 (1H, m) 4.49 (1H, m) 4.52 (1H, m) 5.42 (1H, m, NH) 7.05 (1H, m, NH) 7.55 (1H, m, NH) 7.83 (1H, m, NH).

Example 5

Production of [5S-(tert-butoxycarbonylamino)-4R,6R-dihydroxy-2R-(2-methylpropyl)heptanoyl]-L-valyl-L-methionine 4-fluorobenzylamide (TLVM-9)

(Step 1)

2R-[5S-(tert-Butoxycarbonylamino)-2,2-dimethyl-6R-methyl-1,3-dioxan-4R-yl]methyl-4-methylpentanoyl-L-valyl-L-methionine 4-fluorobenzylamide (compound 26)

The title compound (0.16 g) was obtained from the compound 22 (0.08 g, 0.21 mmol) and H-Val-Met-NH-p-F-Bn in the same way as in the synthesis of the compound 15.

¹H-NMR (CDCl₃) δ: 0.85 (3H, d, J=6 Hz) 0.87 (3H, d, J=6 Hz) 0.92 (3H, d, J=7 Hz) 0.94 (3H, d, J=7 Hz) 1.09 (3H, d, J=7 Hz) 1.18 (1H, m) 1.33 (3H, s) 1.34 (3H, s) 1.44 (9H, s) 1.58 (1H, m) 1.79 (1H, m) 1.84 (1H, m) 1.98 (1H, m) 2.04-2.17 (3H, m) 2.07 (3H, s) 2.39 (1H, m) 2.44-2.63 (2H, m) 3.35 (1H, m) 3.57 (1H, m) 4.07 (1H, m) 4.12 (1H, m) 4.31-4.45 (2H, m) 4.60 (1H, m) 4.73 (1H, d, J=10 Hz, NH) 6.20 (1H, m, NH) 6.75 (1H, m, NH) 6.83 (1H, m, NH) 6.95-7.03 (2H, m) 7.20-7.28 (2H, m).
(Step 2)

[5S-(tert-Butoxycarbonylamino)-4R,6R-dihydroxy-2R-(2-methylpropyl)heptanoyl]-L-valyl-L-methionine 4-fluorobenzylamide (TLVM-9)

The title compound (0.09 g, 0.13 mmol, 64% in 2 steps) was obtained from the compound 26 (0.16 g) in the same way as in the synthesis of the TLVM-5.

¹H-NMR (CDCl₃-CD₃OD) δ: 0.87 (3H, d, J=6 Hz) 0.90 (3H, d, J=7 Hz) 0.91 (3H, d, J=7 Hz) 0.91 (3H, d, J=7 Hz) 1.16 (3H, d, J=6 Hz) 1.26 (1H, m) 1.45 (9H, s) 1.47-1.58 (2H, m) 1.68-1.81 (2H, m) 1.93 (1H, m) 2.05-2.24 (2H, m) 2.08 (3H, s) 2.43-2.52 (3H, m) 3.22 (1H, m) 3.64 (1H, m) 4.12 (1H, d, J=7 Hz) 4.26 (1H, m) 4.33 (1H, d, J=15 Hz) 4.38 (1H, d, J=15 Hz) 4.50 (1H, dd, J=8, 6 Hz) 5.52 (1H, m, NH) 6.97-7.04 (2H, m) 7.20 (1H, m, NH) 7.21-7.36 (2H, m) 7.73 (1H, m, NH) 7.83 (1H, m, NH).

Example 6

Production of [5S-(tert-butoxycarbonylamino)-4R,6R-dihydroxy-2R-(2-methylpropyl)heptanoyl]-L-alanyl-L-methionine benzylamide (TLVM-10)

(Step 1)

2R-[5S-(tert-Butoxycarbonylamino)-2,2-dimethyl-6R-methyl-1,3-dioxan-4R-yl]methyl-4-methylpentanoyl-L-alanyl-L-methionine benzylamide (compound 27)

The title compound (0.04 g, 0.06 mmol, 55%) was obtained from the compound 22 (0.04 g, 0.11 mmol) and H-Ala-Met-NH-Bn in the same way as in the synthesis of the compound 15.

¹H-NMR (CDCl₃) δ: 0.85 (3H, d, J=7 Hz) 0.86 (3H, d, J=6 Hz) 1.09 (3H, d, J=7 Hz) 1.16 (1H, m) 1.31 (3H, s) 1.32 (3H, s) 1.36 (3H, d, J=7 Hz) 1.44 (9H, s) 1.57 (1H, m) 1.74 (1H, m) 1.86 (1H, m) 1.98 (1H, m) 2.03 (1H, m) 2.05 (3H, s) 2.12 (1H, m) 2.33 (1H, m) 2.43-2.58 (2H, m) 3.33 (1H, m) 3.56 (1H, m) 4.08 (1H, m) 4.34 (1H, m) 4.42 (2H, m) 4.59 (1H, m) 4.82 (1H, d, J=10 Hz, NH) 6.28 (1H, m, NH) 6.88 (1H, m, NH) 7.00 (1H, m, NH) 7.17-7.34 (5H, m).

(Step 2)

[5S-(tert-Butoxycarbonylamino)-4R,6R-dihydroxy-2R-(2-methylpropyl)heptanoyl]-L-alanyl-L-methionine benzylamide (TLVM-10)

The title compound (0.01 g, 0.016 mmol, 27%) was obtained from the compound 27 (0.04 g) in the same way as in the synthesis of the TLVM-5.

$^1$H-NMR (CDCl$_3$-CD$_3$OD) δ: 0.91 (3H, d, J=6 Hz) 0.95 (3H, d, J=6 Hz) 1.18 (3H, d, J=6 Hz) 1.33 (1H, m) 1.46 (9H, s) 1.48 (3H, d, J=7 Hz) 1.55-1.83 (3H, m) 1.99 (1H, m) 2.06 (3H, s) 2.07 (1H, m) 2.10 (1H, m) 2.29 (1H, m) 2.46-2.53 (2H, m) 3.38 (1H, m) 3.52 (1H, m) 4.19 (1H, m) 4.34-4.46 (2H, m) 4.47-4.62 (2H, m) 7.21-7.38 (5H, m).

Example 7

Production of [5S-(tert-butoxycarbonylamino)-4R, 6R-dihydroxy-2R-(2-methylpropyl)heptanoyl]-L-phenylglycyl-L-methionine benzylamide (TLVM-11)

(Step 1)

2R-[5S-(tert-Butoxycarbonylamino)-2,2-dimethyl-6R-methyl-1,3-dioxan-4R-yl]methyl-4-methylpentanoyl-L-phenylglycyl-L-methionine benzylamide (compound 28)

The title compound (0.12 g, 0.17 mmol, 79%) was obtained from the compound 22 (0.13 g, 0.35 mmol) and H-Phg-Met-NH-Bn in the same way as in the synthesis of the compound 15.

$^1$H-NMR (CDCl$_3$-CD$_3$OD) δ: 0.89 (3H, d, J=7 Hz) 0.92 (3H, d, J=7 Hz) 1.14 (3H, d, J=6 Hz) 1.24 (1H, m) 1.34 (3H, s) 1.42 (3H, s) 1.43 (9H, s) 1.48-1.62 (2H, m) 1.65-1.80 (2H, m) 1.98 (1H, m) 2.07 (3H, s) 2.14 (1H, m) 2.40-2.55 (3H, m) 3.22 (1H, m) 3.60 (1H, m) 4.05 (1H, m) 4.26-4.37 (3H, m) 4.53 (1H, m) 7.05-7.25 (10H, m).

(Step 2)

[5S-(tert-Butoxycarbonylamino)-4R,6R-dihydroxy-2R-(2-methylpropyl)heptanoyl]-L-phenylglycyl-L-methionine benzylamide (TLVM-11)

The title compound (0.06 g, 0.09 mmol, 51%) was obtained from the compound 28 (0.12 g, 0.17 mmol) in the same way as in the synthesis of the TLVM-5.

$^1$H-NMR (CDCl$_3$-CD$_3$OD) δ: 0.88 (3H, d, J=6 Hz) 0.92 (3H, d, J=6 Hz) 1.14 (3H, d, J=6 Hz) 1.23 (1H, m) 1.44 (9H, s) 1.47-1.62 (2H, m) 1.64-1.76 (2H, m) 1.97 (1H, m) 2.07 (3H, s) 2.16 (1H, m) 2.44-2.55 (3H, m) 3.22 (1H, m) 3.60 (1H, m) 4.21 (1H, m) 4.27-4.40 (3H, m) 4.57 (1H, m) 7.16-7.40 (10H, m).

Example 8

Study on γ-Secretase Inhibitory Effect-(I)

(1) Test Method

HEK293 cells (ATCC) were transfected with APP C99 pcDNA3.1 (the nucleotide sequence of its coding region is shown in SEQ ID NO: 1) (J. Biol. Chem., 2003, 278, 49448-49458). Cell strains (C99 cells) confirmed to stably express APP-C99 (artificial APP fragment that originally lacked a polypeptide portion to be cleaved by α- or β-secretase at the first stage in the two-stage reaction of Aβ production from APP) were used to study the γ-secretase inhibitory effects of four test substances (TLVM-5, TLVM-7, TLVM-8, and TLVM-9) in vitro.

In the present test, a medium used for the C99 cells was 500 mL of a Dulbecco's Modified Eagle's Medium (DMEM, Sigma-Aldrich Corp.) supplemented with 55 ml of fetal bovine serum (Biosource), 5.5 ml of MEM non-essential amino acids (Gibco), and 5.5 ml of penicillin/streptomycin (Gibco).

The C99 cells were suspended at a concentration of $5 \times 10^4$ cells/ml in the medium. The suspension was added at a concentration of 1 ml ($5 \times 10^4$ cells)/well to a 24-well collagen plate (Akita Sumitomo Bakelite Co., Ltd.) and cultured for 3 days. Then, the medium in the wells was removed, and the wells were washed with a medium (1 ml/well). The medium was removed, and a fresh medium was then added thereto at a concentration of 0.4 ml/well. The cells were exposed to the test substances and positive controls and incubated for 24 hours, and the culture supernatants were collected. The positive controls used were L-685,458 (CALBIOCHEM) and Boc-Leu-Val-Met-Leu-OMe (hereinafter, referred to as LVML-1) disclosed in Example 1 of Patent Document 1 (WO03/091278). The exposure concentrations were set to four concentrations, 0.3, 1, 3, and 10 μmol/L, for all the test substances and the positive controls. The concentrations of Aβ (1-40) and Aβ (1-42) in the culture supernatants were measured using Human Amyloid β (1-40) (N) Assay Kit (L)-IBL and Human Amyloid β (1-42) (N) Assay Kit (L)-IBL (Immuno-Biological Laboratories, Co., Ltd.). The amounts of Aβ (1-40) and Aβ (1-42) secreted were calculated by subtracting the concentrations of Aβ (1-40) and Aβ (1-42) originally contained in the medium before the C99 cell inoculation, from the measured concentrations thereof, respectively. Moreover, when the Aβ secretion rate of a negative control (5% DMSO-containing medium, resulting in 1% DMSO at the final concentration) is defined as 100%, Aβ secretion rates at each concentration of the test substances and the positive controls were calculated.

(2) Results

As shown in Tables 1 to 3, the TLVM-5, TLVM-7, TLVM-8, and TLVM-9 exhibited a γ-secretase inhibitory effect much stronger than those of the positive controls L-685,458 and LVML-1.

Moreover, Example 6 of Patent Document 1 (WO03/091278) shows that a Thr-Leu-Val-Met-type compound (1'a) had an Aβ40 production inhibitory rate (exposure concentration: 10 μM) of 73%. On the other hand, as shown in Table 1, the TLVM-5, TLVM-7, TLVM-8, and TLVM-9 brought about an Aβ40 secretion rate (exposure concentration: 10 μM) of 3% or less (97% or more in terms of the inhibitory rate) and further retained activities that brought about a secretion rate of 24% or less (76% or more in terms of the inhibitory rate) even in the lower concentration range (exposure concentration: 0.3 μM). This demonstrated that the compound of the present invention exhibits a much more excellent γ-secretase inhibitory effect than those of the conventional compounds.

TABLE 1

Aβ (1-40) secretion rate (%) of C99 cells brought about by addition of each test substance

|  |  | Exposure concentration (μmol/L) | | | |
|---|---|---|---|---|---|
|  |  | 0.3 | 1 | 3 | 10 |
| Inhibitor | L-685, 458 | 101 | 68 | 38 | 9 |
|  | LVML-1 | 140 | 112 | 106 | 83 |
|  | TLVM-5 | 10 | 5 | 4 | 3 |
|  | TLVM-7 | 24 | 8 | 1 | 3 |
|  | TLVM-8 | 7 | 1 | 2 | 1 |
|  | TLVM-9 | 16 | 8 | 5 | 3 |

TABLE 2

Aβ (1-42) secretion rate (%) of C99 cells brought about by addition of each test substance

|  |  | Exposure concentration (μmol/L) | | | |
|---|---|---|---|---|---|
|  |  | 0.3 | 1 | 3 | 10 |
| Inhibitor | L-685, 458 | 96 | 70 | 49 | 24 |
|  | LVML-1 | 95 | 78 | 104 | 61 |
|  | TLVM-7 | 15 | 55 | 67 | 0 |
|  | TLVM-8 | 7 | 11 | 61 | 0 |
|  | TLVM-9 | 2 | 11 | 37 | 0 |

TABLE 3

Aβ [(1-40) + (1-42)] secretion rate (%) of C99 cells brought about by addition of each test substance

|  |  | Exposure concentration (μmol/L) | | | |
|---|---|---|---|---|---|
|  |  | 0.3 | 1 | 3 | 10 |
| Inhibitor | L-685, 458 | 101 | 68 | 39 | 9 |
|  | LVML-1 | 138 | 110 | 105 | 82 |
|  | TLVM-5 | 14 | 8 | 7 | 6 |
|  | TLVM-7 | 23 | 10 | 4 | 2 |
|  | TLVM-8 | 7 | 1 | 5 | 1 |
|  | TLVM-9 | 15 | 8 | 7 | 3 |

Example 9

Study on γ-Secretase Inhibitory Effect-(II)

(1) Test Method

The TLVM-5, TLVM-7, TLVM-8, and TLVM-9 confirmed in Example 8 to have strong inhibitory activities against γ-secretase activities were subjected to an additional experiment at low concentrations (exposure concentrations were set to three concentrations, 0.03, 0.1, and 0.3 mmol/L, for the test substances and to four concentrations, 0.1, 0.3, 1, and 3 μmol/L, for the positive control).

Moreover, Aβ secretion rates at two concentrations of the test substance that bracket the concentration at which Aβ secretion was inhibited by 50% ($IC_{50}$) were used to calculate $IC_{50}$ according to the following equation:

$$IC_{50} : 10^{[LOG(A/B)*(50-C)/(D-C)+LOG(B)]}, \text{wherein}$$

A: of the two points that bracket 50% inhibition, the higher concentration of the test substance,
B: of the two points that bracket 50% inhibition, the lower concentration of the test substance,
C: secretion rate (%) at the concentration B, and
D: secretion rate (%) at the concentration A.

(2) Results

As shown in Tables 4 to 6, the TLVM-5, TLVM-7, TLVM-8, and TLVM-9 exhibited an excellent γ-secretase inhibitory effect even in the low concentration range (0.03 to 0.3 μmol/L).

The $IC_{50}$ of the test substances (TLVM-5, TLVM-7, TLVM-8, and TLVM-9) against Aβ (1-40) and Aβ (1-42) were 0.033 to 0.089 μmol/L (positive control: 1.8 μmol/L) and 0.11 to 0.29 μmol/L (positive control: 1.7 μmol/L), respectively, and exhibited an effect much stronger than that of the positive control.

TABLE 4

Aβ (1-40) secretion rate (%) of C99 cells brought about by addition of each test substance

|  |  | Exposure concentration (μmol/L) | | | | | $IC_{50}$ |
|---|---|---|---|---|---|---|---|
|  |  | 0.03 | 0.1 | 0.3 | 1 | 3 | (μmol/L) |
| Inhibitor | L-685, 458 | — | 114 | 90 | 72 | 32 | 1.8 |
|  | TLVM-5 | 100 | 39 | 15 | — | — | 0.080 |
|  | TLVM-7 | 124 | 42 | 13 | — | — | 0.089 |
|  | TLVM-8 | 53 | 16 | 7 | — | — | 0.033 |
|  | TLVM-9 | 94 | 32 | 17 | — | — | 0.070 |

TABLE 5

Aβ (1-42) secretion rate (%) of C99 cells brought about by addition of each test substance

|  |  | Exposure concentration (μmol/L) | | | | | $IC_{50}$ |
|---|---|---|---|---|---|---|---|
|  |  | 0.03 | 0.1 | 0.3 | 1 | 3 | (μmol/L) |
| Inhibitor | L-685, 458 | — | 97 | 91 | 87 | 8 | 1.7 |
|  | TLVM-5 | 131 | 74 | 43 | — | — | 0.23 |
|  | TLVM-7 | 156 | 94 | 33 | — | — | 0.22 |
|  | TLVM-8 | 71 | 52 | 33 | — | — | 0.11 |
|  | TLVM-9 | 97 | 67 | 49 | — | — | 0.29 |

TABLE 6

Aβ [(1-40) + (1-42)] secretion rate (%) of C99 cells brought about by addition of each test substance

|  |  | Exposure concentration (μmol/L) | | | | | $IC_{50}$ |
|---|---|---|---|---|---|---|---|
|  |  | 0.03 | 0.1 | 0.3 | 1 | 3 | (μmol/L) |
| Inhibitor | L-685, 458 | — | 113 | 90 | 73 | 31 | 1.8 |
|  | TLVM-5 | 101 | 40 | 16 | — | — | 0.082 |
|  | TLVM-7 | 126 | 44 | 14 | — | — | 0.092 |
|  | TLVM-8 | 54 | 17 | 8 | — | — | 0.034 |
|  | TLVM-9 | 94 | 33 | 18 | — | — | 0.072 |

Example 10

Measurement of Cytotoxicity (1) Test Method

The cytotoxicity of four test substances (TLVM-5, TLVM-7, TLVM-8, and TLVM-9) on the C99 cells was measured using a method shown below.

In the present test, a medium used for the C99 cells was 500 mL of a Dulbecco's Modified Eagle's Medium (DMEM, Sigma-Aldrich Corp.) supplemented with 55 ml of fetal bovine serum (Biosource), 5.5 ml of MEM non-essential amino acids (Gibco), and 5.5 ml of penicillin/streptomycin (Gibco).

The C99 cells were suspended at a concentration of $0.75 \times 10^5$ cells/ml in the medium. The suspension was added at a concentration of 100 μL ($0.75 \times 10^4$ cells)/well to a 96-well collagen plate (Akita Sumitomo Bakelite Co., Ltd.) and cultured for 2 days. Then, the medium (corresponding to 50 μL/well) in the wells was removed, and a fresh medium was added thereto at a concentration of 30 μL/well. The cells were exposed to the test substances (20 μL/well; final concentration: 0.3, 1, 3, 10, 30, and 100 mmol/L) for 24 hours. Then, the cell viability was measured using Cell Counting Kit-8 (Dojindo Laboratories).

(2) Results

As shown in Table 7, all the inhibitors at the exposure concentrations (10 μmol/L or lower) used in Examples of the present invention were confirmed to cause no reduction in cell viability, although some test substances at the concentrations of 30 μmol/L or higher reduced the cell viability. It was thus concluded that the inhibitory effect confirmed in the present Examples on γ-secretase activities is not attributed to the cytotoxicity of the test substances.

TABLE 7

Cell viability (%) of C99 cells brought about by addition of each test substance

| | | Exposure concentration (μmol/L) | | | | | |
|---|---|---|---|---|---|---|---|
| | | 0.3 | 1 | 3 | 10 | 30 | 100 |
| Inhibitor | L-685, 458 | 133 | 125 | 110 | 99 | — | — |
| | TLVM-5 | 102 | 109 | 112 | 104 | 82 | 46 |
| | TLVM-7 | 92 | 105 | 96 | 102 | 91 | 96 |
| | TLVM-8 | 101 | 102 | 101 | 98 | 91 | 8 |
| | TLVM-9 | 104 | 106 | 106 | 105 | 93 | 57 |

Example 11

Study on Substrate Specificity (1) Test Method

Of families constituting human Alcadein (hereinafter, referred to as Alc) known as a substrate for γ-secretase to colocalize with APP in brain neurons, an artificial Alcα fragment (hereinafter, referred to as Alcα C150) whose first extracellular cleavage site and γ-secretase cleavage site were determined was used to study the substrate specificity of the γ-secretase inhibitor of the present invention. β-Alcα produced from a first cleavage construct of Alcα cannot be quantified by sELISA used in Aβ measurement. Therefore, proteins with an attached FLAG tag at the N termini of first cleavage constructs of Alcα and of C99 were expressed by cells. FLAG-Aβ-like peptides secreted into a medium were collected by immunoprecipitation using anti-FLAG antibodies and detected by western blotting using the antibodies. A specific method thereof is shown below.

HEK293 cells (ATCC) ($1 \times 10^7$ cells/10 cm dish) cultured in 6 ml of 10% FCS-containing DMEM (Wako Pure Chemical Industries, Ltd.) were transfected with FLAG APP C99 pcDNA3.1 (the nucleotide sequence of its coding region is shown in SEQ ID NO: 2) (J. Biol. Chem., 2003, 278, 49448-49458 (which was prepared from pcDNA3-APPC99)) or with FLAG Alcα C150 pcDNA3.1 (the nucleotide sequence of its coding region is shown in SEQ ID NO: 3) (J. Biol. Chem., 2004, 279, 24343-24354 (which was the same as pcDNA3AlcαΔE)) using Lipofectamine 2000 (Invitrogen Corp.) according to the protocol included in the reagent. Each inhibitor and a positive control (γ-Secretase Inhibitor IX (DAPT)) (Calbiochem Contact Information) were separately added at a concentration of 0.2 or 2 μmol/L. The same dose of DMSO (Wako Pure Chemical Industries, Ltd.) thereas was added as a negative control. 24 hours later, the culture supernatants were collected, and samples were preliminarily purified using beads (100 μL of 50% (v/v) Protein-G Sepharose (GE Healthcare)). Then, 15 μL of 50% (v/v) anti-FLAG antibody M2 beads (Sigma-Aldrich Corp.) were added thereto, and the samples were incubated at 4° C. for 1 hour. The beads were collected by centrifugation and washed three times with a buffer (10 mM Tris-HCl [pH 8.0], 140 mM NaCl, 0.1% n-octyl glucoside, 0.025% sodium azide), and Aβ and β-Alcα in the medium were collected. The proteins were subjected to SDS-PAGE using a 15% Tris-Tricine gel (Anal Biochem., 1987, 166 (2), 368-379) and then transferred to a membrane. The membrane was boiled for 5 minutes in PBS. Then, anti-FLAG M2 antibodies (5 μg/ml) (Sigma-Aldrich Corp.) were added thereto, and the membrane was incubated, followed by detection using a western blotting detection reagent ECL (GE Healthcare). This signal was quantified using Versa-doc system (Bio-Rad Laboratories, Inc.) to calculate protein secretion rates (the protein secretion rate of the negative control is defined as 100%).

(2) Results

As shown in Tables 8 and 9, the TLVM-5, TLVM-7, TLVM-8, TLVM-9, and TLVM-11 at the concentration of 0.2 μmol/L and the TLVM-10 at the concentration of 2 μmol/L, when allowed to act on the cells, did not inhibit the γ cleavage of the Alcα-C150 and specifically inhibited the cleavage of APP-C99.

The compound of the present invention was confirmed to have the specific inhibitory effect in the particular concentration range and therefore, was considered to serve as a useful therapeutic drug for Alzheimer's disease.

TABLE 8

Aβ and β-Alcα secretion rates (%) of HEK293 cells brought about by addition of each test substance (0.2 μmol/L)

| | Inhibitor | | | | | |
|---|---|---|---|---|---|---|
| | DAPT | TLVM-5 | TLVM-7 | TLVM-8 | TLVM-9 | TLVM-11 |
| (i) Aβ | 8 | 41 | 36 | 32 | 43 | 8 |
| (ii) β-Alc α | 23 | 140 | 120 | 118 | 158 | 68 |
| (i)/(ii) ratio | 0.35 | 0.29 | 0.30 | 0.27 | 0.27 | 0.12 |

TABLE 9

Aβ and β-Alcα secretion rates (%) of HEK293 cells brought about by addition of each test substance (2 μmol/L)

| | Inhibitor | |
|---|---|---|
| | DAPT | TLVM-10 |
| (i) Aβ | 20 | 37 |
| (ii) β-Alc α | 16 | 94 |
| (i)/(ii) ratio | 1.26 | 0.39 |

The invention claimed is:

1. A compound of the following formula (1) or a pharmaceutically acceptable salt thereof:

[Formula 1]

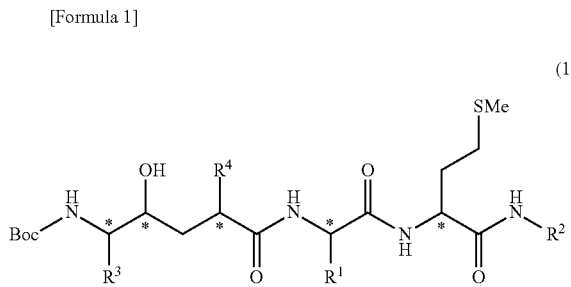

(1)

wherein $R^1$ represents a linear or branched alkyl group having 1 to 4 carbon atoms or a phenyl group; $R^2$ represents a linear or branched alkyl group having 1 to 4 carbon atoms which may be substituted by one or more phenyl or halogenophenyl groups; $R^3$ represents a linear or branched alkyl group having 1 to 4 carbon atoms and having one or more hydroxyl groups; $R^4$ represents a linear or branched alkyl group having 1 to 4 carbon atoms; and the symbol "*" represents a chiral center.

2. The compound according to claim 1, which has a structure of the following formula (2), or a pharmaceutically acceptable salt thereof:

[Formula 2]

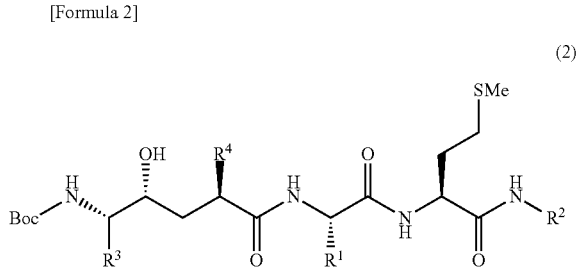

(2)

wherein $R^1$ represents a linear or branched alkyl group having 1 to 4 carbon atoms or a phenyl group; and $R^2$ represents a linear or branched alkyl group having 1 to 4 carbon atoms which may be substituted by one or more phenyl or halogenophenyl groups.

3. The compound according to claim 1, which has a structure of the following formula (3), or a pharmaceutically acceptable salt thereof:

[Formula 3]

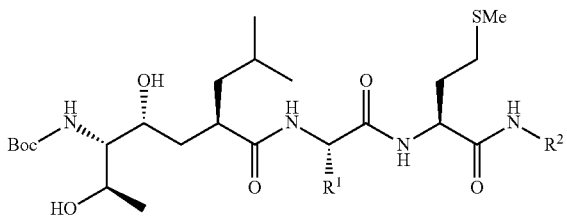

(3)

wherein $R^1$ represents a linear or branched alkyl group having 1 to 4 carbon atoms or a phenyl group; $R^2$ represents a linear or branched alkyl group having 1 to 4 carbon atoms which may be substituted by one or more phenyl or halogenophenyl groups; $R^3$ represents a linear or branched alkyl group having 1 to 4 carbon atoms and having one or more hydroxyl groups; and $R^4$ represents a linear or branched alkyl group having 1 to 4 carbon atoms.

4. A compound selected from the group consisting of:
   [5S-(tert-butoxycarbonylamino)-4R,6R-dihydroxy-2R-(2-methylpropyl)heptanoyl]-L-valyl-L-methionine benzylamide,
   [5S-(tert-butoxycarbonylamino)-4R,6R-dihydroxy-2R-(2-methylpropyl)heptanoyl]L-valyl-L-methionine n-butylamide,
   [5S-(tert-butoxycarbonylamino)-4R,6R-dihydroxy-2R-(2-methylpropyl)heptanoyl]-L-valyl-L-methionine (S)-α-methylbenzylamide,
   [5S-(tert-butoxycarbonylamino)-4R,6R-dihydroxy-2R-(2-methylpropyl)heptanoyl]-L-valyl-L-methionine 4-fluorobenzylamide,
   [5S-(tert-butoxycarbonylamino)-4R,6R-dihydroxy-2R-(2-methylpropyl)heptanoyl]-L-alanyl-L-methionine benzylamide,
   [5S-(tert-butoxycarbonylamino)-4R,6R-dihydroxy-2R-(2-methylpropyl)heptanoyl]-L-phenylglycyl-L-methionine benzylamide; and
   a pharmaceutically acceptable salt thereof.

5. A composition, comprising a compound according to claims 1, 2, 3 or 4 or a pharmaceutically acceptable salt thereof; and a pharmaceutically acceptable carrier.

6. A method for inhibiting γ-secretase in a subject in need thereof, comprising administering to the subject an effective amount of a compound according to claims 1, 2, 3 or 4 or a pharmaceutically acceptable salt thereof.

7. A method for inhibiting amyloid protein production in a subject in need thereof, comprising administering to the subject an effective amount of a compound according to claims 1, 2, 3 or 4 or a pharmaceutically acceptable salt thereof.

* * * * *

SEQUENCE LISTING

<160> NUMBER OF SEQ ID NOS: 3

<210> SEQ ID NO 1
<211> LENGTH: 357
<212> TYPE: DNA
<213> ORGANISM: Homo sapiens

<400> SEQUENCE: 1

```
atgctgcccg ptttggcact gctcctgctg gccgcctgga cggctcgggc ggatgcagat      60
gcagaattcc gacatgactc aggatatgaa gttcatcatc aaaaattggt gttctttgca     120
gaagatgtgg gttcaaacaa aggtgcaatc attggactca tggtgggcgg tgttgtcata     180
gcgacagtga tcgtcatcac cttggtgatg ctgaagaaga acagtacac atccattcat      240
catggtgtgt ggaggttga cgccgctgtc accccagagg agcgccacct gtccaagatg      300
cagcagaacg gctacgaaaa tccaacctac aagttctttg agcagatgca gaactag        357
```

<210> SEQ ID NO 2
<211> LENGTH: 378
<212> TYPE: DNA
<213> ORGANISM: Homo sapiens

<400> SEQUENCE: 2

```
atgctgcccg ptttggcact gctcctgctg gccgcctgga cggctcgggc ggatgcagat      60
gcagaattcc gacatgacta caaggacgac gatgacaagt caggatatga agttcatcat     120
caaaaattgg tgttctttgc agaagatgtg ggttcaaaca aaggtgcaat cattggactc     180
atggtgggcg gtgttgtcat agcgacagtg atcgtcatca ccttggtgat gctgaagaag     240
aaacagtaca catccattca tcatggtgtg tggaggttg acgccgctgt caccccagag      300
gagcgccacc tgtccaagat gcagcagaac ggctacgaaa atccaaccta caagttcttt     360
gagcagatgc agaactag                                                   378
```

<210> SEQ ID NO 3
<211> LENGTH: 570
<212> TYPE: DNA
<213> ORGANISM: Homo sapiens

<400> SEQUENCE: 3

```
gccaccatgc tgcgccgccc cgctcccgcg ctggccccgg ccgccggct gctgctggcc       60
gggctgctgt gcggcggcgg ggtctgggcc gattacaagg atgatgatga caagttcgtg     120
cacccggaac accgctcctt tgttgacctg tcaggccaca acctggccaa ccccacccg      180
ttcgcagtcg tccccagcac tgcgacagtt gtgatcgtgg tgtgcgtcag cttcctggtg     240
ttcatgatta tcctgggggt atttcggatc cgggccgcac atcggcggac catgcgggat     300
```

```
caggacaccg ggaaggagaa cgagatggac tgggacgact ctgccctgac catcaccgtc    360
aaccccatgg agacctatga ggaccagcac agcagtgagg aggaggagga agaggaagag    420
gaagaggaaa gcgaggacgg cgaagaagag gatgacatca ccagcgccga gtcggagagc    480
agcgaggagg aggagggga gcagggcgac ccccagaacg caacccggca gcagcagctg    540
gagtgggatg actccaccct cagctactga                                    570
```